United States Patent
McLeay

(10) Patent No.: US 12,239,719 B2
(45) Date of Patent: Mar. 4, 2025

(54) FLUOROCHEMICAL TARGETED THERAPIES

(71) Applicant: MT RESEARCH, LLC, San Diego, CA (US)

(72) Inventor: Matthew T. McLeay, Omaha, NE (US)

(73) Assignee: MT RESEARCH, LLC, San Diego, CA (US)

( * ) Notice: Subject to any disclaimer, the term of this patent is extended or adjusted under 35 U.S.C. 154(b) by 38 days.

(21) Appl. No.: 17/681,596

(22) Filed: Feb. 25, 2022

(65) Prior Publication Data

US 2022/0175972 A1 Jun. 9, 2022

Related U.S. Application Data

(62) Division of application No. 16/302,011, filed as application No. PCT/US2017/032965 on May 16, 2017, now abandoned.

(60) Provisional application No. 62/455,163, filed on Feb. 6, 2017, provisional application No. 62/336,843, filed on May 16, 2016.

(51) Int. Cl.

| A61K 49/00 | (2006.01) |
|---|---|
| A61K 31/02 | (2006.01) |
| A61K 31/08 | (2006.01) |
| A61K 31/135 | (2006.01) |
| A61K 31/4045 | (2006.01) |
| A61K 31/496 | (2006.01) |
| A61K 31/517 | (2006.01) |
| A61K 31/695 | (2006.01) |
| A61K 31/7004 | (2006.01) |
| A61K 31/7068 | (2006.01) |
| A61K 33/00 | (2006.01) |
| A61K 38/06 | (2006.01) |
| A61K 38/39 | (2006.01) |
| A61K 39/395 | (2006.01) |
| A61K 41/00 | (2020.01) |
| A61K 45/06 | (2006.01) |
| A61K 47/24 | (2006.01) |
| A61K 51/02 | (2006.01) |
| A61N 5/06 | (2006.01) |
| A61P 35/00 | (2006.01) |
| A61P 35/04 | (2006.01) |
| C07K 16/28 | (2006.01) |
| A61K 39/00 | (2006.01) |
| A61N 5/067 | (2006.01) |

(52) U.S. Cl.
CPC .......... *A61K 49/0036* (2013.01); *A61K 31/02* (2013.01); *A61K 31/08* (2013.01); *A61K 31/135* (2013.01); *A61K 31/4045* (2013.01); *A61K 31/496* (2013.01); *A61K 31/517* (2013.01); *A61K 31/695* (2013.01); *A61K 31/7004* (2013.01); *A61K 31/7068* (2013.01); *A61K 33/00* (2013.01); *A61K 38/06* (2013.01); *A61K 38/39* (2013.01); *A61K 39/3955* (2013.01); *A61K 41/0057* (2013.01); *A61K 45/06* (2013.01); *A61K 47/24* (2013.01); *A61K 49/0032* (2013.01); *A61K 49/0056* (2013.01); *A61K 49/0058* (2013.01); *A61K 49/0076* (2013.01); *A61K 51/02* (2013.01); *A61N 5/062* (2013.01); *A61P 35/00* (2018.01); *A61P 35/04* (2018.01); *C07K 16/2863* (2013.01); *A61K 2039/505* (2013.01); *A61N 2005/0664* (2013.01); *A61N 5/067* (2021.08); *C07K 2317/21* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| 4,781,676 | A | 11/1988 | Schweighardt et al. |
|---|---|---|---|
| 4,865,836 | A | 9/1989 | Long, Jr. |
| 4,987,154 | A | 1/1991 | Long, Jr. |
| 5,149,319 | A | 9/1992 | Unger |
| 5,531,219 | A | 7/1996 | Rosenberg |
| 5,655,521 | A | 8/1997 | Faithfull et al. |
| 6,136,346 | A | 10/2000 | Elijamal et al. |
| 6,139,819 | A | 10/2000 | Unger et al. |
| 8,980,227 | B2 | 3/2015 | Somerville et al. |
| 9,351,942 | B2 | 5/2016 | Nishimura et al. |
| 9,351,943 | B2 | 5/2016 | McLeay |
| 9,925,144 | B2 | 3/2018 | Fabio et al. |

(Continued)

FOREIGN PATENT DOCUMENTS

| CN | 106551909 A | 4/2017 |
|---|---|---|
| WO | 9628090 A1 | 9/1996 |

(Continued)

OTHER PUBLICATIONS

"Baglole et al (Immunological Investigations, 2006, vol. 35, pp. 297-325) (Year: 2006)".
"Final Office Action Received for U.S. Appl. No. 17/054,087, mailed on Aug. 11, 2022."
"Harrison and Blackwell (The Oncologist, 2004, vol. 9, suppl. 5, pp. 31-40) (Year: 2004)".
"Non Final Office Action received for U.S. Appl. No. 16/712,150, Mailed on Sep. 16, 2022."
"The abstract of Campas et al (Drugs of the Future, 2008, vol. 33, pp. 649-654) (Year: 2008)".

(Continued)

*Primary Examiner* — Jennifer Chin
(74) *Attorney, Agent, or Firm* — Kutak Rock LLP; Ryan S. Hinderliter

(57) ABSTRACT

The present invention is directed to compositions and methods targeting cells in a subject harboring conditions or at risk for conditions that would benefit from gas-based diagnostic and therapy. The present invention relates to the use of fluorochemical compositions and methods of delivery that result in retention of the fluorochemical composition and any bioactive agent, including gaseous substances, delivered in combination with the fluorochemical composition.

25 Claims, 2 Drawing Sheets

(56) References Cited

U.S. PATENT DOCUMENTS

| | | | |
|---|---|---|---|
| 10,543,273 | B2 | 1/2020 | McLeay |
| 10,874,687 | B1 | 12/2020 | Sommadossi et al. |
| 11,446,244 | B2 | 9/2022 | McLeay |
| 11,918,598 | B2 | 3/2024 | McLeay |
| 12,083,178 | B2 | 9/2024 | McLeay |
| 2003/0013675 | A1 | 1/2003 | Yeadon et al. |
| 2004/0038856 | A1 | 2/2004 | Chakravarty et al. |
| 2005/0049359 | A1 | 3/2005 | Keipert et al. |
| 2006/0159658 | A1 | 7/2006 | Deo et al. |
| 2007/0117788 | A1 | 5/2007 | Yeadon |
| 2007/0258908 | A1 | 11/2007 | Lanza et al. |
| 2010/0297033 | A1 | 11/2010 | McLeay |
| 2010/0312312 | A1 | 12/2010 | Jones |
| 2010/0324276 | A1 | 12/2010 | Sundaram et al. |
| 2011/0048420 | A1 | 3/2011 | Gibbins et al. |
| 2011/0056492 | A1 | 3/2011 | Longest et al. |
| 2012/0076777 | A1 | 3/2012 | McLeay |
| 2012/0264646 | A1 | 10/2012 | Link et al. |
| 2014/0190496 | A1 | 7/2014 | Wensley et al. |
| 2016/0317660 | A1 | 11/2016 | McLeay |
| 2018/0369422 | A1 | 12/2018 | Haber et al. |
| 2018/0369513 | A1 | 12/2018 | Hannon et al. |
| 2020/0114006 | A1 | 4/2020 | McLeay |
| 2020/0215065 | A1 | 7/2020 | Irwin et al. |
| 2020/0368263 | A1 | 11/2020 | Dempsey et al. |
| 2020/0368297 | A1 | 11/2020 | Chen et al. |
| 2021/0040135 | A1 | 2/2021 | Kim et al. |
| 2021/0069098 | A1 | 3/2021 | McLeay |
| 2021/0196776 | A1 | 7/2021 | Cho et al. |
| 2021/0220265 | A1 | 7/2021 | McLeay |
| 2021/0228485 | A1 | 7/2021 | McLeay |
| 2021/0299258 | A1 | 9/2021 | McLeay |
| 2023/0018580 | A1 | 1/2023 | McLeay |
| 2024/0252525 | A1 | 8/2024 | McLeay |

FOREIGN PATENT DOCUMENTS

| | | |
|---|---|---|
| WO | 98005301 A1 | 2/1998 |
| WO | 9924016 A1 | 5/1999 |
| WO | 2007025244 A2 | 3/2007 |
| WO | 2007139827 A2 | 12/2007 |
| WO | 2012003457 A1 | 1/2012 |
| WO | 2015168080 A1 | 11/2015 |
| WO | 2017085692 A1 | 5/2017 |
| WO | 2017201089 A1 | 11/2017 |
| WO | 2018112040 A1 | 6/2018 |
| WO | 2018220376 A1 | 12/2018 |
| WO | 2019104038 A1 | 5/2019 |
| WO | WO2019/217413 A1 | 11/2019 |
| WO | 2021154687 A1 | 8/2021 |

OTHER PUBLICATIONS

Tschulakow, Alexander, et al. Effects of a Single Intravitreal Injection of Aflibercept and Ranibizumab on Glomeruli of Monkeys; Nov. 21, 2014; PLOS One 9(11); pp. 1-20.

Journal of Clinical Investigation, 2007, vol. 117, (pp. 524-529).

Miller, et al., "First-in-human intraoperative near-infrared fluorescence imaging of glioblastoma using cetuximab-IRDye800", Journal of Neuro-Oncology, Springer US, New York,, vol. 139, No. 1, Apr. 6, 2018 (Apr. 6, 2018), pp. 135-143, XP036539275.

Zhang, et al., "Perfluorocarbon-based nanomedicine: emerging strategy for diagnosis and treatment of diseases", MRS Communications, vol. 8, No. 2, Apr. 5, 2018 (Apr. 5, 2018), pp. 303-313, XP055915683.

Lee, et al., "Synthesis, characterization, and biological verification of anti-HER2 indocyanine green-doxorubicin-loaded polyethyleneimine-coated perfluorocarbon double nanoemulsions for targeted photochemotherapy of breast cancer cells", Journal of Nanobiotechnology, (2017) 15:41, pp. 1-17.

Kazuhide, et al, Near infrared photoimmunotherapy in the treatment of disseminated peritoneal ovarian cancer Mol Cancer Ther., Jan. 2015, pp. 141-150, vol. 14, No. 1.

Mitsunaga et al. , Cancer Cell-Selective In Vivo Near Infrared Photoimmunotherapy Targeting Specific Membrane Molocules "Nat Med, 2012, pp. 1685-1691, vol. 17, No. 12".

Ohanlon et al. , "NIR-labeled perfluoropolyether nanoemulsions for drug delivery and imaging", Journal of Fluorine Chemistry, Elsevier, NL, vol. 137, Feb. 7, 2012 (Feb. 7, 2012), pp. 27-33.

Rafailov et al. , "Proc. of SPIE, Feb. 2015, Conference Paper, vol. 9303, 93030W-13".

Sato et al. , "Mol Cancer Ther., Jan. 2015, pp. 141-150, vol. 14, No. 1".

Tschulakow et al. , "PLOS One, Nov. 21, 2014, pp. 1-20".

Wynn , "Journal of Clinical Investigation, 2007, vol. 117, pp. 524-529)".

Zhang , et al., ""Perfluorocarbon-based nanomedicine: emerging strategy for diagnosis and treatment of diseases", MRS Communications, vol. 8, No. 2, Apr. 5, 2018 (Apr. 5, 2018), pp. 303-313, XP055915683,", ISSN: 2159-6859, DOI: 10.1557/mrc.2018.49.

"Notice of Allowance Received for Canadian Patent Application No. 3104821 Mailed on Mar. 28, 2024."

"Notice of Allowance received for U.S. Appl. No. 16/712,150, Mailed on May 8, 2024".

"Final Office Action Received for U.S. Appl. No. 17/054,087, mailed on Jun. 26, 2023".

"Final Office Action received for U.S. Appl. No. 16/712,150, Mailed on Feb. 28, 2024".

"Examiner's Report Received for Canadian Patent Application No. 3104821 Mailed on Jun. 21, 2023."

"Communication Pursuant to Article 94(3) EPC Received for EP Application No. 17800041.0 mailed on Jan. 22, 2024."

"Non-Final Office Action received for U.S. Appl. No. 16/712,150, Mailed on Mar. 16, 2023.", 12 Pages.

Coley , et al., "Perfluorocarbon-Enhanced Sonography: Value in Detecting Acute Venous Thrombosis in Rabbits", AJR: 163 961-964; Oct. 1994, Oct. 1994, 4 Pages.

Cosco , "Perfluorocarbon-loaded micro and nanosystems for medical imaging: A state of the art; Journal of Fluorine Chemistry", 171 (2015) 18-26, 9 Pages.

"Communication Pursuant to Article 94(3) EPC received for EP Application No. 17800041.0 mailed on May 12, 2022."

"Non-Final Office Action received for U.S. Appl. No. 16/712,150, Mailed on Sep. 13, 2023".

Franki , et al., "Boiling histotripsy lesion characterization on a clinical magnetic resonance imaging-guided high intensity focused ultrasound system", PLOS One, Mar. 16, 2017, pp. 1-23.

Martin , et al., "Current Status and Prospects for Microbubbles in Ultrasound Theranostics", Wiley Interdiscip Rev Nanomed Nanobiotechnol 2013; 5(4), pp. 1-25.

Wenjin , et al., "Preparation and Evaluation of Poly (L-lactide-co-glycolide)(PLGA) Microbubbles as a Contrast Agent for Myocardial Contrast Echocardiography", Wiley Interscience, Jan. 27, 2005, pp. 1-8.

Xu , "Controlled ultrasound tissue erosion", The role of dynamic interaction between insonation and microbubble activity; J Acoust Soc Am. Jan. 2005; 117(1): 424-435, pp. 1-26.

"Examiner's report received for CA Patent Application No. 3104821 Mailed on Nov. 23, 2022."

"Non-Final Office Action Received for U.S. Appl. No. 17/054,087, mailed on Dec. 22, 2022."

"Communication Pursuant to Article 94(3) EPC Received for EP Patent Application No. 19800615.7 , Mailed on Aug. 30, 2023".

Yuhao , et al., "Perfluorocarbon nanoparticles enhance reactive oxygen levels and tumour growth inhibition in photodynamic therapy, Nature Communications", vol. 6, Nov. 3, 2015 (Nov. 3, 2015), pp. 1-8, XP055398740, DOI: 1 0.1 038/ncomms9785.

"Abrahamse and Hamblin, Biochem J., Feb. 15, 2016, pp. 347-364, vol. 473, No. 4".

"Centis et al (Artificial Organs, 2007, vol. 31, pp. 649-653)".

"Chappelow and Kaiser (Drugs, 2008, vol. 68, pp. 1 029-1 036)".

"Communication pursuant to Rules 70(2) and 70a(2) EPC received for EP Application No. 17800041.0 on Jan. 28, 2020".

"Confocal laser endomicroscopy, Gastrointestinal Endoscopy, 2014, pp. 929-938, vol. 80, No. 6"

"Drug Facts and ComparisonsTM (1999, pp. 3285-3300)".

(56) References Cited

OTHER PUBLICATIONS

"Entry for "Aerosols". The National Library of Medicine MeSH thesaurus. <meshb.nlm.nih.gov/record/ui?ui=D000336> Accessed Jun. 6, 2021. (Year: 2021)".
"Entry for "Emulsions". The National Library of Medicine MeSH thesaurus. <meshb.nlm.nih.gov/record/ui?ui=D004655> Accessed Jun. 6, 2021. (Year: 2021)".
"Examination Report Received for Canada Patent Application No. 3104821, mailed on Mar. 23, 2022."
"Extended European Search Report received for EP application 17800041.0, mailed on Jan. 8, 2020".
"Extended European Search Report Received for EP Application No. 19800615.7 Mailed on May 9, 2022".
"Final Office Action Received for U.S. Appl. No. 16/302,011, mailed on Jun. 25, 2020."
"Final Office Action Received for U.S. Appl. No. 15/144,418, mailed on May 15, 2019, 8 pages".
"Final Office Action Received for U.S. Appl. No. 16/302,011, mailed on Nov. 26, 2021."
"Gioni et al (Molecular Cancer Research, 2008, vol. 5, pp. 706-714)"
"International Preliminary Report on Patentability received for PCT Application No. PCT/US2017/032965 dated Sep. 14, 2017".
"International Search Report and Written Opinion for International Application No. PCT/US19/31106, Search completed Aug. 2, 2016, Mailed Aug. 2, 2019, 20 Pages", 20.
"International Search Report and Written Opinion received for PCT Application No. PCT/US2011/42815 dated Nov. 3, 2011".
"International Search Report and Written Opinion Received for PCT Application No. PCT/US2017/032965 on Sep. 14, 2017."
"Modi et al. (Breast Cancer Research and Treatment, 2005, vol. 90, pp. 157-163)".
"Non-Final Action received for U.S. Appl. No. 16/302,011, Mailed on Jun. 10, 2021."
"Non Final Office Action received for U.S. Appl. No. 16/302,011, Mailed on Feb. 6, 2020, pp. 7".
"Non-Final Office Action Received for U.S. Appl. No. 17/054,087, mailed on Feb. 17, 2022."
"Non-Final office action received for U.S. Appl. No. 13/175,305 dated Apr. 30, 2015".
"Non-Final office action received for U.S. Appl. No. 13/175,305 dated Aug. 1, 2014".
"Non-Final office action received for U.S. Appl. No. 15/144,418 dated Jul. 19, 2018".
"Non-Final office action received for U.S. Appl. No. 15/144,418 dated Oct. 6, 2017".
"Notice of Allowance Received for U.S. Appl. No. 15/144,418, mailed on Sep. 12, 2019, 19 pages".
"Notice of Allowance received for U.S. Appl. No. 13/175,305 dated Feb. 3, 2016".
"Pilarek M. Liquid perfluorochemicals as flexible and efficient gas carriers applied in bioprocess engineering: an updated overview and future prospects. 2014 Chem. Process Eng. 35: 463-487. (Year: 2014)".
"Song et al. "Hypoxia-Associated Resistance in Cancer Therapies" Nano Letters. Sep. 13, 2016 (Sep. 13, 2016) vol. 16, p. 6145-6153; entire document".
"Stroncek and Puri, Journal of Translational Medicine, 2010, vol. 8, No. 31, pp. 1-2."
"Thomas and O'Brien, Journal Compilation, Apr. 22, 2009, pp. 887-889, vol. 104".
"Ye et al. Synthesis and evaluation of new iRGD peptide analogs for tumor optical imaging. 2011 Bioorg. Med. Chem. Lett. 21: 1146-1150. (Year: 2011)".
Agostinis et al., "CA Cancer J Clin., 2011, pp. 250-281, vol. 61, No. 4".
Awwad, Sahar, et al., "Overview of Antibody Drug Delivery, Pharmaceutics, Mar. 27, 2018, 10, 83, doi:10.3390/pharmaceutics 10030083".
Bergholt et al., "Gastroenterology, 2014, pp. 27-32, vol. 146".

Cheng et al., "Nature Communications, Nov. 3, 2015, pp. 1-8, vol. 6, No. 8785".
Cunderlikova et al., "Biochimica et Biophysica Acta 1840, 2014, pp. 2702-2708".
Day et al., "Preclinical Comparison of Near-Infrared-Labeled Cetuximab and Panitumumab for Optical Imaging of Head and Neck Squamous Cell Carcinoma", Molecular Imaging & Biology, vol. 15, No. 6, May 29, 2013 (May 29, 2013), pp. 722-729.
Giraudeau et al., "19F molecular MR imaging for detection of brain tumor angiogenesis: in vivo validation using targeted PFOB nanoparticles", Angiogenesis, Kluwer Academic Publishers, Do, vol. 16, No. 1, Oct. 6, 2012 (Oct. 6, 2012), pp. 171-179.
Hanaoka et al., "Nanomedicine (Lond)., Apr. 2015, pp. 1139-1147, vol. 10 No. 7".
Haque et al., "Lung, Oct. 4, 2016, pp. 945-957, vol. 194".
Kamuhabwa et al., "Enhancing the photodynamic effect of hypericin in human bladder transitional cell carcinoma spheroids by the use of the oxygen carrier, perfluorodecalin", International Journal of Oncology, vol. 28, Mar. 1, 2006 (Mar. 1, 2006), pp. 775-780.
Kil et al., "Antitumor Activities of Hypericin as a Protein Tyrosine Kinase Blocker", Archives of Pharmacal Research, Natl. Fisheries University, Pusan, KR, vol. 19, No. 6, Dec. 1, 1996 (Dec. 1, 1996), pp. 490-496.
Lee, et al., ""Synthesis, characterization, and biological verification of anti-HER2 indocyanine green-doxorubicin-loaded polyethyleneimine-coated perfluorocarbon double nanoemulsions for targeted photochemotherapy of breast cancer cells", Journal of Nanobiotechnology,", vol. 15, No. 1, Dec. 1, 2017 (Dec. 1, 2017), p. 41, XP055915672, DOI: 10.1186/s12951-017-0274-5.
Lui et al., "Arch Dermatol, 2004, pp. 26-32, vol. 140".
Menaa et al., ""Development of carbon-fluorine spectroscopy for pharmaceutical and biomedical applications", 1 page abstract, 2011".
Miller, et al., "First-in-human intraoperative near-infrared fluorescence imaging of glioblastoma using cetuximab-IRDye800", Journal of Neuro-Oncology, Springer US, New York,, vol. 139, No. 1, Apr. 6, 2018 (Apr. 6, 2018), pp. 135-143, XP036539275,, ISSN: 0167-594X, DOI: 10.1007/S11060-018-2854-0 [retrieved on Apr. 6, 2018].
"Bliss, Susan J., "Ribavirin: Understanding the Long-Term Side Effects"; Aug. 15, 2018, p. 1-12".
"Derwent abstract for CN 106551909A (2017)".
"Final Office Action Received for U.S. Appl. No. 17/151,191, mailed on May 24, 2021".
"Final Office Action Received for U.S. Appl. No. 17/231,735, mailed on Feb. 9, 2022."
"Final Office Action received for U.S. Appl. No. 17/947,711, Mailed on Aug. 24, 2023".
"Govorkova and Webster, Combination Chemotherapy for Influenza, Viruses, pp. 1510-1529, 2010, 2".
"Highlights of Prescribing Information for Copegus (ribavirin) Tablets; Revised Aug. 2011, Genentech, Inc."
"Machine-assisted English translation for CN 106551909A (2017)".
"Martinez, Miguel Angel, Compounds with Therapeutic Potential against Novel Respiratory 2019 Coronavirus, May 2020, pp. 1-7, vol. 64, issue 5".
"Non-Final Action received for U.S. Appl. No. 17/151,191, Mailed on Apr. 1, 2021".
"Non-Final Action received for U.S. Appl. No. 17/151,191, mailed on Jan. 31, 2022."
"Non-Final Action received for U.S. Appl. No. 17/231,735, Mailed on May 27, 2021".
"Non-Final Action received for U.S. Appl. No. 17/231,735, Mailed on Sep. 22, 2021".
"Non-Final Office Action Received for U.S. Appl. No. 17/947,711, mailed on Apr. 27, 2023."
"Non-Final Office Action Received for U.S. Appl. No. 17/054,087, mailed on Jun. 21, 2024".
"Notice of Allowance received for U.S. Appl. No. 17/151,191, Mailed on Jun. 8, 2022".
"Notice of Allowance Received for U.S. Appl. No. 17/947,711, mailed on Oct. 25, 2023."

(56) References Cited

OTHER PUBLICATIONS

"Renard, Sebastien MD, et al., Severe Pulmonary Arterial Hypertension in Patients Treated for Hepatitis C With Sofosbuvir, 2016 149(3):e69-e73 Chest".

"Respaud et al ("Effect of formulation on the stability and aerosol performance of a nebulized antibody", mAbs, 6:5, p. 1347-1355 (2014), obtained online from the website: https://www.tandfonline.com/doi/pdf/10.4161/mabs.29938). (Year: 2014)".

Barnard, et al., "Enhancement of the infectivity of SARS-CoV in BALB/c mice by IMP dehydrogenase inhibitors, including ribavirin, Antiviral Research, 2006, pp. 53-63, vol. 71".

Donohue, et al., "The Autophagy Inhibitor Verteporfin Moderately Enhances the Antitumor Activity of Gemcitabine in a Pancreatic Ductal Adenocarcinoma Model", Journal of Cancer, vol. 4(7) (2013), p. 585-596) (Year: 2013), Aug. 28, 2013, 12 Pages.

Dumont, et al, "A Novel Inhaled Dry-Powder Formulation of Ribavirin Allows for Efficient Lung Delivery in Healthy Participants and Those with Chronic Obstructive Pulmonary Disease in a Phase 1 Study, Antimicrobial Agents and Chemotherapy, May 2020, pp. 1-15, vol. 64, Is".

Ferron, et al., "Structural and molecular basis of mismatch correction and ribavirin excision from coronavirus RNA, PNAS, Dec. 26, 2017, pp. E162-E171".

Gilbert and McLeay, "MegaRibavirin Aerosol for the Treatment of Influenza A Virus Infections in Mice, Antiviral Res., Jun. 2008, pp. 223-229, vol. 78, issue 3".

Li, et al., "Potential antiviral therapeutics for 2019 Novel Coronavirus, PubMed, Mar. 12, 2020, pp. 170-172, vol. 43 issue 3".

Liu, et al., "Efficacy and safety of antiviral treatment for COVID-19 from evidence in studies of SARS-CoV-2 and other acute viral infections: a systematic review and meta-analysis, CMAJ, Jul. 6, 2020, pp. E734-E744, vol. 192, issue 27".

Messina, Emanuela, et al., ""Ribavirin Aerosol in the Treatment of SARS-CoV-2: A Case Series", Infect Dis Ther (2021) 10:2791-2804".

Tong, et al., "Ribavirin therapy for severe COVID-19: a retrospective cohort study, International Journal of Antimicrobial Agents, 2020, vol. 56".

Wong, et al., "Clinical outcomes of different therapeutic options for COVID-19 in two Chinese case cohorts: A propensity-score analysis, pp. 1-13, EClinicalMedicine 32 (2021)".

FLUOROCHEMICAL TARGETED THERAPIES

CROSS-REFERENCE TO RELATED APPLICATIONS

This application is a divisional application of U.S. patent application Ser. No. 16/302,011, which was filed under 35 USC § 371 on Nov. 15, 2018, as a U.S. national phase application of PCT/US2017/03296517, which was filed on May 16, 2017, which claims the benefit of U.S. Provisional Patent Application No. 62/455,163, filed Feb. 6, 2017, and U.S. Provisional Patent Application No. 62/336,843, filed May 16, 2016, each of which is herein incorporated by reference in its entirety.

FIELD OF THE INVENTION

The present invention generally relates to compositions and methods for the administration of gas-based therapies and/or bioactive agents to a subject in need thereof. In particular, the present invention relates to methods, systems, and compositions comprising fluorochemical composition for use in the delivery of diagnostics and therapies to a target area in a subject that are retained in the target area for a sufficient time to provide a benefit.

BACKGROUND OF THE INVENTION

The use of gas-based therapies has proven useful in accelerating external wound healing and in treating lung conditions and injury. Compositions and methods of exploiting the benefits of gas-based therapies for the treatment of internal ailments has yet to be effectively exploited. Internal ailments that would benefit from gas-based therapies include internal injuries as well as cancer.

Regarding cancer, it has been long known that cancer cells are able to adapt and survive in a variety of microenvironments. For instance, there are some cancer cells that thrive in microenvironments having available oxygen, similar to those of normal cells. Also, there are some cancer cells that thrive in microenvironments lacking oxygen due, in part, to a growth rate that outpaces the establishment of vasculature capable of delivering oxygen. These oxygen deprived cancer cells metabolize glucose by aerobic glycolysis. This phenomenon, known as the Warburg effect, is characterized by increased glycolysis and lactate production regardless of oxygen availability. Aerobic glycolysis is often accompanied by several changes in cell metabolic processes including an increase in glucose and glutamine uptake.

Cancer therapies include targeting these different metabolic processes of cancer cells. However, therapies that alter the availability of oxygen using gas-based therapies in the microenvironment of a cancer cell, or injury site, have yet to be developed. One of the biggest barriers to such gas-based therapies is the delivery and retention of such therapies to an internal target. Fibroblasts and macrophages are cells that are known to associate with cancer referred as stroma and thereby can be used as a surrogate marker of cancer since locating this stroma enables an indirect diagnostic for cancer.

Photodynamic therapy is a subset of gas-based therapy in that light is used to induce the formation of reactive oxygen species in tissues. The formation and maintenance of cell killing levels of reactive oxygen species depends upon the availability of local oxygen. In hypoxic tumors, where oxygen levels are low, additional oxygen may be provided.

Cheng and coworkers (Nature Communications 6:8795, 2015) reported the enhanced killing of endogenous CT26 murine colon adenocarcinomas in mice by administering (intravenous as well as intratumoral injection) the near infrared photosensitizer IR780 with the oxygen-bearing perfluorohexane compared to IR780 alone. However, Cheng and coworkers did not demonstrate anti-stromal activity or a durable anti-cancer response, or visualization and/or targeting of cancer-associated stroma or other support cells.

Near infrared photoimmunotherapy (PIT) is a form of PDT that targets the photosensitizer to the prescribed tissue or cell type. Sato and coworkers (Mol. Cancer Ther. 14(1): 141-150, 2015) demonstrated the reduction of luciferase-based luminescence production by SKOV-3/luc tumors in mice injected with IR700 conjugated with trastuzumab (PIT-treated) compared to IR only (NIR-treated). Both groups were treated with 100 J/cm2 of NIR light at day zero. The PIT-treated mice showed lower relative luminescence units (RLU) compared to NIR-treated mice at day 4 post light treatment, demonstrating some cancer cell reduction in the PIT group. However, by day 14, the RLU of the PIT-treatment group recovered to post-treatment levels. Similarly, Maawy and coworkers (PLOS One, DOI: 10.1371; Mar. 23, 2015) noted 100% recurrence rate of human BxPC-3 pancreatic tumors in an orthotopic mouse model, despite the anti-tumor effects of anti-CEA-IR700-mediated PIT.

Accordingly, a need exists for gas-based diagnostics and therapeutics, and the delivery thereof with efficacy and target site retention, and enhanced and long-term PDT killing of tumors. The compositions and methods of the present invention provide such gas-based diagnostics and therapeutics and therapeutic delivery with efficacy and target site retention, and enhanced PDT tumor killing and post-surgical site sterilization.

The inventor has achieved durable anti-tumor activity by inhibiting or killing tumor stromal cells (including e.g., cancer-associated fibroblasts and macrophages) by contacting those cells with a perfluorocarbon. By combining the perfluorcarbon with a near infrared photosensitizer linked to or combined with an anti-cancer antibody, drug, or chemotherapeutic, durable and enhanced anti-tumor activity is achieved.

SUMMARY OF THE INVENTION

In one aspect, the invention provides compositions and methods of targeting, detecting, and/or killing disease cells in a subject harboring conditions or at risk for conditions that would benefit from therapy including gas-based therapy or photodynamic therapy.

Some embodiments of the invention provide the use of fluorochemical compositions containing a perfluorocarbon molecule, a near infrared dye or other fluorescently detectable label conjugated to a targeting molecule or therapeutic molecule to detect and/or ablate diseased tissue or cells, such as cancer cells and supporting stroma, or fibrotic tissue.

Some embodiments of the invention provide methods of delivery of the subject fluorochemical composition to a patient having a cancer, a fibrosis, or other disease in need of treatment. In some embodiments, the fluorochemical composition is administered intravenously, peritumorally, intratumorally, or, per os, followed by the administration of light to the target tissues or cells. In some embodiments, the light therapy is applied before a tumor is disturbed to allow the formation of reactive oxygen species in the target cells and subsequent apoptosis to occur, after which time, the target cells are excised or biopsied.

In one aspect, the invention provides diagnostic and theranostic methods for detecting and treating cancer and fibroses by administering compositions containing a fluorochemical, a fluorophore and optionally a targeting agent.

In one aspect, the invention provides a method for treating cancer or pre-cancerous tissues such as hyperplasias and dysplasias by administering a subject fluorochemical composition, such as an antibody-NIR conjugate combined with a perfluorocarbon.

DRAWINGS

DETAILED DESCRIPTION

Figure 1:
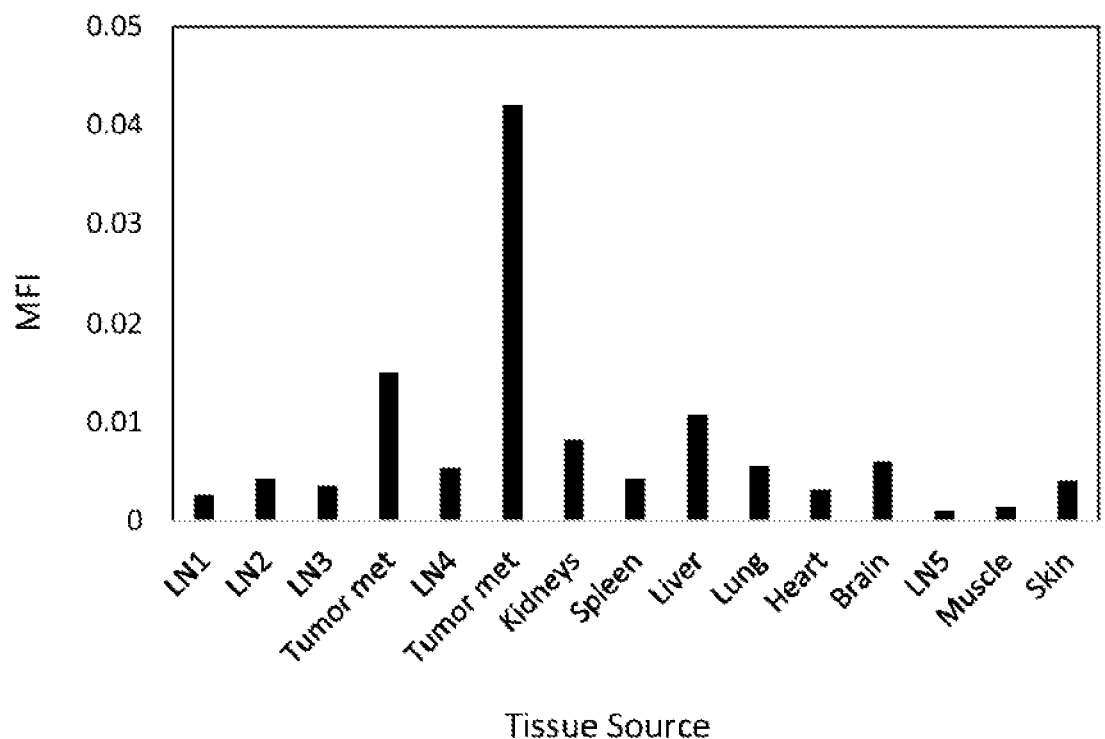
FIG. 1 depicts a bar histogram depicting mean fluorescence intensity in arbitrary units at 700 nm as a function of tissue uptake of perflubron. The X-axis depicts tissues, where LN=lymph node.

In accordance with the present invention, a composition that is capable of delivering gas-based therapy and/or bioactive agents as well as methods of use have been discovered. The invention finds use in targeting cells in a subject harboring conditions or at risk for conditions that would benefit from such a therapy. In particular, the invention relates to the use of fluorochemical compositions for use as a delivery mechanism to targeted tissue and cells that results in retention of the fluorochemical composition and permits visualizing same along with any therapeutic agent, including gaseous substances and bioactive agents, delivered in combination with the fluorochemical composition.

I. COMPOSITIONS

Compounds useful in this invention, such as those listed below (hereinafter called "fluorocarbons" or "fluorochemicals" or "perflubron" or "perfluorocarbons") are generally able to promote gas exchange, and most of these fluorocarbons readily dissolve gaseous substances, including but not limited to oxygen or carbon dioxide.

A. Fluorocarbons

Fluorocarbon molecules used in the present invention may have various structures, including straight or branched chain or cyclic structures as known in the art. These molecules may also have some degree of unsaturation, and may also contain bromine or hydrogen atoms, or they may be amine derivatives. Typically, the fluorocarbon is a liquid or a gas at room temperature (25° C.). Preferably, the fluorocarbon has from about 2, 3, 4, or 5 carbon atoms to about 10, 12, or 14 carbon atoms. There are a number of fluorocarbons that are contemplated for use in the present invention. These fluorocarbons include but are not limited to bis(F-alkyl) ethanes such as $C_4F_9CH=CH_4CF_9$ (sometimes designated "F-44E"), i-$C_3F_9$ CH=CH$C_6F_{13}$ ("F-i36E"), and $C_6F_{13}CH=CHC_6F_{13}$ ("F-66E") cyclic fluorocarbons, such as C10F18 ("F-decalin", "perfluorodecalin" or "FDC"), F-adamantane ("FA"), F-methyladamantane ("FMA"), F-1,3-dimethyladamantane ("FDMA"), F-di- or F-trimethylbicyclo[3,3,1]nonane ("nonane"); perfluorinated amines, such as F-tripropylamine ("FTPA") and F-tri-butylamine ("FTBA"), F-4-methyloctahydroquinolizine ("FMOQ"), F-n-methyl-decahydroisoquinoline ("FMIQ"), F-n-methyldecahydroquinoline ("FHQ"), F-n-cyclohexylpurrolidine ("FCHP"), F-2-butyltetrahydrofuran ("FC-75" or "RM101") and other fluorocarbons known in the art.

Other fluorocarbons include brominated perfluorocarbons, such as but not limited to 1-bromo-heptadecafluorooctane ($C_8F_{17}Br$, sometimes designated perfluorooctylbromide or "PFOB"), 1-bromopenta-decafluoroheptane ($C_7F_{15}Br$), and 1-bromotridecafluorohexane ($C_6F_{13}Br$, sometimes known as perfluorohexylbromide or "PFHB"). Other brominated fluorocarbons are disclosed in U.S. Pat. No. 3,975,512 to Long. Also contemplated are fluorocarbons having nonfluorine substituents, such as perfluorooctyl chloride, perfluorooctyl hydride, and similar compounds having different numbers of carbon atoms.

Additional fluorocarbons contemplated in accordance with this invention include perfluoroalkylated ethers or polyethers, such as but not limited to $(CF_3)_2 CFO(CF_2CF_2)_2 OCF(CF_3)_2$, $(CF_3)_2 CFO—(CF_2CF_2)_3OCF(CF_3)$, $(CF_3)CFO (CF_2CF_2)F$, $(CF_3)_2 CFO(CF_2CF_2)_2F$, $(C_6F_{13})_2O$. Further, fluorocarbon-hydrocarbon compounds, such as, for example compounds having the general formula $C_nF_{2n+1}—C_nF_{2n'+1}$, $C_nF_{2n+1}OC_nF_{2n'+1}$, or $Cn F_{2n+1}CF=CHC_nF_{2n'+1}$, where n and n' are the same or different and are from about 1 to about 10 (so long as the compound is a liquid at room temperature). Such compounds, for example, include but are not limited $C_8F_{17}C_2H_5$ and $C_6F_{13}CH=CHC_6H_{13}$. It will be appreciated that esters, thioethers, and other variously modified mixed fluorocarbon-hydrocarbon compounds are also encompassed within the broad definition of "fluorocarbon" materials suitable for use in the present invention. Mixtures of fluorocarbons are also contemplated. Additional "fluorocarbons" not listed herein, but having those properties described in this disclosure that would lend themselves to use in accordance with the present invention are additionally contemplated.

The fluorocarbons used in the present invention may be used as neat liquid compositions, as gases, or as emulsions.

B. Fluorocarbon Emulsions

In one embodiment, the fluorocarbon compositions of the present invention will include an emulsifying agent to create a fluorocarbon emulsion. Such emulsions are typically fluorocarbon-in-water emulsions having a discontinuous fluorocarbon phase and a continuous aqueous phase. In an additional embodiment, emulsions with a continuous fluorocarbon phase and a discontinuous aqueous phase are also contemplated. The emulsions typically include any emulsifying agents used or known in the industry including but not limited to, osmotic agents, buffers, electrolytes and combinations thereof.

Although fluorocarbon concentrations from about 1% to 5% are possible and contemplated as low as 0.5% w/v are also possible. In another embodiment the concentrations of fluorocarbon are about 5% to at least 25% or 30%, preferably at least 40%, 50%, 55%, and may be 60%, 75% or 80% w/v. In an additional embodiment emulsions containing up to 85%, 90%, 100%, and 125% fluorocarbon are also contemplated. Preferred fluorocarbon emulsion formulations are known in the art and include without limitation those disclosed in U.S. Pat. Nos. 4,865,836; 4,987,154; 4,927,623; and 6,204,296 which are hereby incorporated by reference.

1. The Emulsifying Agent

The fluorocarbon emulsions can also include an emulsifying agent. As used in this specification, an emulsifying agent is any compound or composition that aids in the formation and maintenance of the droplets of the discontinuous phase by forming a layer at the interface between the discontinuous and continuous phases. The emulsifying agent may comprise a single compound or any combination of compounds, such as in the case of co-surfactants.

In the present invention, emulsifying agents can include compounds known in the industry but are not limited to phospholipids, nonionic surfactants, fluorinated surfactants, which can be neutral or anionic, and combinations of such emulsifying agents. Lecithin is a phospholipid that has frequently been used as a fluorocarbon emulsifying agent, as is more fully described in U.S. Pat. No. 4,865,836. Another example of an emulsifying agent for use with fluorochemical compositions is egg yolk phospholipids. See e.g., Long, U.S. Pat. No. 4,987,154.

Other emulsifying agents may be used with good effect, such as fluorinated surfactants, also known as fluorosurfactants. Fluorosurfactants that can provide stable emulsions include triperfluoroalkylcholate; perfluoroalkylcholestanol; perfluoroalkyloxymethylcholate; $C_3F_7 O(CF_2)_3C(=O)NH(CH_2)_3N(O)(CH_3)_2$ (XMO-10); and fluorinated polyhydroxylated surfactants, such as, for example, those discussed in "Design, Synthesis and Evaluation of Fluorocarbons and Surfactants for In Vivo Applications New Perfluoroalkylated Polyhydroxylated Surfactants" by J. G. Riess, et al. J. G. Riess et al., Biomat. Artif. Cells Artif. Organs 16: 421-430 (1988).

The nonionic surfactants suitable for use in the present invention include polyoxyethylene-polyoxypropylene copolymers. An example of such class of compounds is Pluronic, such as Pluronic F-68. Anionic surfactants, particularly fatty acids (or their salts) having 12 to 24 carbon atoms, may also be used. One example of a suitable anionic surfactant is oleic acid, or its salt, sodium oleate.

It will be appreciated by one of ordinary skill in the art that choice of a particular emulsifying agent is not central to the present invention. A number of emulsifying agents can be used and will depend on the target, fluorochemical, and bioactive agents used. Indeed, virtually any emulsifying agent (including those still to be developed) capable of facilitating formation of a fluorocarbon-in-water emulsion can form improved emulsions when used in the present invention. The optimum emulsifying agent or combination of emulsifying agents for a given application may be determined through routine empirical studies that do not require undue experimentation. Consequently, one practicing the art of the present invention should choose the emulsifying agent or combination of emulsifying agents for such properties as biocompatibility.

2. Preparation of the Emulsion

Fluorocarbon emulsions according to the invention are prepared by means of conventional emulsification procedures, such as, for example, mechanical or ultrasonic emulsification of an emulsion formulation in a Manton-Gaulin mixer or Microfluidizer (Microfluidics Corp., Newton, Mass.). Any means known in the industry for creating an emulsion can be used.

Usually, a pre-emulsion mixture is prepared by simple mixing or blending of the various components. This pre-emulsion is then emulsified in the desired emulsification apparatus.

The combined fluorocarbon concentration in the emulsion is preferably anywhere within the range of about 20% to about 125% (w/v). In another embodiment the fluorocarbon concentration is 5% to about 20%. In preferred emulsions, the total perfluorocarbon concentration is from about 30%, 40%, or 50% to about 70%, 80%, 90%, or 100% (w/v).

Emulsifiers are added in concentrations of from about 0.1% to 10%, more preferably 1% or 2% to about 6% (w/v).

The fluorocarbon can act to inhibit NfkB activation to aide in diminishing tumor progression (metastasis). In one embodiment, the fluorocarbon composition alone is the therapeutic agent. In certain embodiments, the fluorochemical composition is used in combination with at least one gas-based therapeutic. In certain embodiments, the fluorochemical composition is used in combination with at least one bioactive agent. In other embodiments, the fluorocarbon composition may be combined or co-administered with at least one gas-based therapeutic and at least one bioactive agent. In certain embodiments, more than one bioactive agent or gas-based therapeutic may be combined with the fluorocarbon composition. Such compounds may be administered to the subject simultaneously or sequentially. A fluorochemical composition of the invention may be administered to a subject in conjunction with at least a second compound known in the art to benefit treating the target microenvironment. The amount of gas or bioactive agent administered to a subject in conjunction with a fluorochemical composition will depend on the desired dosage prescribed to treat the target.

The fluorochemical will penetrate throughout the tumor. The uptake of the fluorochemical into the tumor stroma will allow identification or visualization of the tumor and simultaneously inhibit the same tumor macrophages and fibroblasts. Further, the fluorochemical can be combined with an amount of another bioactive agent administered before, during, or after administrating the fluorochemical so as to aid the delivery of the bioactive agent to the tumor or desired location for treatment. Penetration of these agents aids in overall treatment of a patient. The specific perfluorooctyl bromide (neat or emulsified), also known as perflubron, has demonstrated anti-macrophage and anti-fibroblast activity. International Patent Application No. WO2012003457A1 is incorporated herein for teaching the anti-fibroblastic activity of the perfluorocarbon perfluorooctyl bromide.

C. Gas-Based Therapy

In one embodiment, the fluorocarbon composition is combined with a gas. Suitable gases include any therapeutic, bioactive, or diagnostic gas or gas composition known in the art or yet to be discovered, as well as combinations thereof, that may be administered to a subject. The precise amount of gas used in combination with the composition of the present invention is dependent upon the target, the agent of choice, the required dose, and the specific nature of the gas that is actually combined with the composition. Those skilled in the art will appreciate that such determinations may be made by using well known techniques in combination with the teachings of the present invention.

Preferred gas and gas compositions may comprise, but are not limited to oxygen, carbon dioxide, nitrogen, helium, hydrogen sulphide, nitric oxide, neon, argon, krypton, xenon, radon, sulfur hexafluoride, carbon monoxide, hydrogen, chlorine, fluorine, ethane, and combinations thereof.

D. Bioactive Agents

In one embodiment, the fluorocarbon composition is combined with a bioactive compound. Suitable bioactive agents include any therapeutic, bioactive, or diagnostic compound or composition known in the art or yet to be discovered, as well as combinations thereof, that may be administered to a subject. In certain embodiments, the bioactive agent is at least one metabolic inhibitor, chemotherapy agent, radiation agent, beneficial agent, or a combination thereof. The precise amount of bioactive agent used in combination with the composition of the present invention is dependent upon the target, the agent of choice, the required dose, and the form of the agent actually combined with the composition. Those skilled in the art will appreciate that such determinations may be made by using well known techniques in combination with the teachings of the present invention.

1. Metabolic Inhibitors

Metabolic inhibitors include bioactive molecules capable of affecting metabolic processes relied upon by cancer or pre-cancerous cells. Inhibition of these pathways aide in blocking the tumors fuel. Any metabolic process affecting molecule known in the art or yet to be discovered is contemplated herein. Suitable metabolic processes that may be affected include, without limitation, nucleic acid synthesis, amino acid metabolism, protein synthesis, lipid synthesis, glycolysis, mitochondrial metabolism, TCA cycle, fatty acid metabolism, glycolytic, NAD metabolism, phosphoinositide 3-kinase signal transduction and any other metabolic process relied upon by cancer or pre-cancerous cells. Suitable nucleic acid synthesis inhibitors include, without limitation, methotrexate, pemetrexed, 5-fluorouracil, hydroxyurea, gemcitabine, fludarabine, ribose synthesis inhibitors (i.e. transketolawe-like protein 1 and glucose-6-phosphate dehydrogenase inhibitors), folate metabolism inhibitors, thymidine synthesis inhibitors, deoxynucleotide synthesis inhibitors, and nucleotide incorporation inhibitors. Suitable amino acid metabolism/protein synthesis inhibitors include, without limitation, L-asparaginase, arginine deiminase conjugated to polyethylene glycol, glutamine inhibitors, and phosphoglycerate dehydrogenase inhibitors. Suitable lipid synthesis inhibitors include fatty acid synthase inhibitors, ATP citrate lyase inhibitors, and acetyl-CoA carboxylase inhibitors. Suitable glycolysis inhibitors include 2-deoxyglucose, 2-deoxy-D-glucose, 2-deoxy-2-[18f]fluoro-D-glucose, glucose transport inhibitors, phosphofructokinase 2 inhibitors, phosphoglycerate mutase inhibitors, pyruvate kinase M2 inhibitors, lactate dehydrogenase A inhibitors, and lactate excretion inhibitors. Suitable mitochondrial metabolism inhibitors include dichloroacetate (DCA), isocitrate dehydrogenase inhibitors, malic enzyme inhibitors, mitochondrial complex I inhibitors, metformin, glutamine availability inhibitors, and pyruvate carboxylase inhibitors. Suitable fatty acid metabolism inhibitors may include monoacylglyceral lipase inhibitors and carnitine palmitoyltransferase 1C inhibitors. Suitable NAD metabolism inhibitors may include nicotinamide phosphoribosyltransferase (NAMPT) inhibitors such as bMPC-9528. Additional effectors of metabolic processes include, without limitation, insulin-like growth factor inhibitors, mTOR inhibitors such as rapamycin, VEGF inhibitors such as avastin, and HIF1-alpha inhibitors such as PX-478.

2. Chemotherapy Agents

Exemplary embodiments of chemotherapy agents include, without limitation, actinomycin D (Cosmegen), aldesleukin (Proleukin), alitretinoin (Panretin), all-trans retinoic acid/ATRA (Tretinoin), altretamine (Hexalen), amascrine, asparaginase (Elspar), azacitidine (Vidaza), azathioprine (Imuran), bacillus calmette-guerin/BCG (TheraCys, TICE BCG, TICE), bendamustine hydrochloride (Treanda), bexarotene (Targretin), bicalutamide (Casodex), bleomycin (Blenoxane), bortezomib (Velcade), busulfan (Busulfex, Myleran), capecitabine (Xeloda), carboplatin (Paraplatin), carmustine bcnu (BiCNU), chlorambucil (Leukeran), cisplatin/cisplatinum (Platinol, Platinol-AQ), cladribine (Leustatin), cyclophosphamide/cytophosphane (Cytoxan, Endoxan, Neosar, Procytox, Revimmune), cytabarine (Cytosar-U), dacarbazine (DTIC-Dome), daunorubicin/daunomycin (DaunoXome, Cerubidine), denileukin diftitox (Ontak), dexrazoxane (Zinecard), docetaxel (Taxotere), melphalen, doxorubicin (Adriamycin, Rubex), doxorubicin (Doxil), doxorubicin liposomal (Doxil), epirubicin (Ellence), etoposide (Eposin, Etopophos, Toposar, Vepesid, VP-16), fludarabine (Fludara), fluorouracil 5-FU (Adrucil), gemcitabine (Gemzar), goserelin (Zolodex), hydrocortisone (Solu-Cortef), hydroxyurea (Hydrea), idarubicin (Idamycin), ifosfamide (Ifex, Mitoxana), interferon alfa (Intron-A, Roferon-A), irinotecan CPT-11 (Camptosar), lapatinib (Tykerb), lenalidomide (Revlimid), leuprolide (Eligard, Lupron, Lupron Depot, Viadur), mecholorethamine/chlormethine/mustine/HN2 (Mustargen), mercaptopurine (Purinethol), methotrexate (Rheumatrex), methylprednisolone (Solu-Medrol), mitomycin (Mutamycin), mitotane (Lysodren), mitoxantrone (Novantrone), octreotide (Sandostatin, Sandostatin LAR), oprelvekin (Neumega), oxaliplatin (Eloxatin, Oxaliplatin Medac), paclitaxel (Taxol, Onxal), paclitaxel protein-bound (Abraxane), pamidronate (Aredia), pazopanib (Votrient), pegaspargase (Oncospar), pegfilgrastim (Neulasta), PEG interferon (PEG-INTRON), Pemetrexed (Alimta), Pentostatin (Nipent), Phenylalanine mustard (Alkeran), plicamycin/mithramycin (Mithracin), prednisone (Deltasone, Liquid Pred, Meticorten, Orasone), prednisolone (Delta-Cortef, Orapred, Pediapred, Prelone), procarbazine (Matulane), raloxifene (Evista), romiplostim (Nplate), sargramostim (Leukine), sorafenib (Nexavar), streptozocin (Zanosar), sunitinib (Sutent), tamoxifen (Novaldex), temozolomide (Temodar), temsirolimus (Torisel), teniposide (Vumon, VM-26), thalidomide (Thalomid), thioguanine (Thioguanine Tabloid), thiophosphoamide/thiotepa (Thioplex), thiotepa (Thioplex), topotecan hydrochloride (Hycamtin), toremifene (Fareston), tretinoin (Vesanoid), valrubicin (Valstar), vinblastine (Velban, Alkaban-AQ), vincristine (Oncovin, Vincasar, Vincrex), vindesine (Eldisine), vinorelbine (Navelbine), vorinostat (Zolinza), and zoledronic acid (Zometa). In addition, heated intraperitoneal chemotherapy (HIPEC) can be used.

Chemotherapy agents also include antibody-based therapies including, without limitation, alemtuzumab (Campath), bevacizumab (Avastin), cetuximab (Erbitux), gemtuzumab ozogamicin (Mylotarg), ibritumomab tiuxetan (Zevalin), ofatumumab (Arzerra), panitumumab (Vectibix), rituximab (Rituxan, Mabthera), tositumomab (Bexxar), trastuzumab (Herceptin), and trastuzumab DM1 (Herceptin DM1). In some embodiments, monoclonal antibodies are combined with dyes such as near infrared dyes (IRDye) or other similar fluorescent agents.

Further, chemotherapy agents include tyrosine-kinase inhibitor (TKI) based therapies including, without limitation, axitinib, afatinib, regorafenib, bafetinib, bosutinib, cediranib (Recentin), crizotinib, dasatinib (Sprycel), erlotinib hydrochloride (Tarceva), gefitinib (Iressa), imatinib (Gleevec, Glivec), lapatinib (Tykerb/Tyverb), lestaurtinib, neratinib, nilotinib (Tasigna), nintedanib, ponatinib, quizartinib, regorafenib, ruxolitinib, sunitibin (Sutent), tofacitinib, vandetanib (Zactima), N-acetylcysteine, and vatalanib. In addition the anti-cancer agent can include anti-virals including by not limited to Ribavirin. In some embodiments, the TKI is combined with fluorescent or other molecules, which enables multi-targeting of stroma and cancer cells.

3. Radiation Agents

Exemplary embodiments of radiation agents include radiation based therapies such as external radiation, brachytherapy, systemic radiation, use of radiosensitizers and radioprotecters, and carbon ion beams. By way of example, radiation based therapies may include, without limitation, x-rays, gamma rays, antibody targeted radiation, seed implant radiation, and other radiation therapies known in the art or yet to be discovered. Antibody targeted radiation may include ibritumomab tiuxetan (Zevalin), tositumomab and iodine-131 (Bexxar), samarium-153 lexidronan (Quadramet), strontium-89 chlorine (Metastron), and others known in the art or yet to be discovered.

4. Beneficial Agents

Exemplary beneficial agents may comprise but are not limited to respiratory agents, antibodies, antibiotics, antivirals, mydriatics, antiglaucomas, anti-inflammatories, antihistaminetics, antineoplastics, anesthetics, ophthalmic agents, cardiovascular agents, active principles, nucleic acids, genetic material, immunoactive agents, imaging agents, immunosuppressive agents, gastrointestinal agents, hyaluron (HA) and combinations thereof. Further exemplary embodiments of the present invention comprise anti-inflammatory agents such as the glucocorticosteroids (i.e. cortisone, prednisone, prednisolone, dexamethasone, betamethasone, Beclomethasone diproprionate, Triamcinolone actinide, Flunisolide) xanthines (i.e. theophylline, caffeine), antibiotics (i.e. aminoglycosides, penicillins, cephalosporins, macolides, quinolones, tetracyclines, chloramphenicol), bronchodilators such as the $B_2$-agonists (i.e. adrenaline, isoprenaline, salmeterol, albuterol, salbutamol, terbutaline, formoterol) and surfactgants. Still other exemplary embodiments include α/B adrenergic blockers (i.e. Normodyne®, Trandate®), angiotensin converting enzyme inhibitors (i.e. Vasotec®), antiarrhythmics, beta blockers, calcium channel blockers, inotropic agents, vasodilators, vasopressors, anesthetics (i.e. morphine) and ophthalmic agents (i.e. Polymyxin B, Neomycin, Gramicidin).

Beneficial agents may also include collagenases. Any bioactive agent capable of breaking peptide bonds in collagen is contemplated herein. Exemplary collagenases include, without limitation, collagenase *Clostridia histolyticum* (Xiaflex®).

In accordance with the present invention, those skilled in the art will appreciate that various bioactive agents may be used in combination with the compositions of the present invention and selection of the bioactive agents used depends upon the intended use of the invention. Further, those skilled in the art will appreciate that various forms of these compounds may be used to modify the therapeutic index of the bioactive agents.

Because the compositions of the present invention are uniquely suited for use in a wide variety of physiological applications such as ocular, oral, pulmonary, rectal, subcutaneous, intratumoral, intramuscular, intraperitoneal, nasal, vaginal, mucosal (gut tube included esophagus, colon, and the like) or aural administration of medicaments or diagnostic compounds, a wide variety of bioactive agents may be incorporated therein. Accordingly, the foregoing list of bioactive agents is not intended to limit the present invention in any way.

Another advantage provided by the present invention is the ability to use the free base form of the incorporated bioactive agent rather than its less efficacious salt form. That is, the efficacy of lipophilic forms of drugs has been shown in many instances to be more potent than the less lipophilic forms of the agent, (i.e. the salts). The nonreactive nature of the fluorochemical compositions allows the incorporation of particularly efficacious base forms of the selected pharmaceutical agent. As those skilled in the art will appreciate, the use of these more potent agent forms enhances the bioavailability of the incorporated pharmaceutical agent and reduces the dosages which must be administered.

The present invention may optionally contain at least one nonfluorinated co-solvent to facilitate the combination of a bioactive agent in the fluorochemical composition. Preferably, the concentration of the nonfluorinated co-solvent comprises up to about 50% v/v of the fluorochemical composition. Suitable co-solvents include any of those known in the art or yet to be discovered. Exemplary co-solvents include ethers, alcohols, alkyl sulfoxides and combinations thereof. Preferably the co-solvents are short chain alcohols (i.e. carbon chain length ≤4 carbons) or an alkyl sulfoxide such as dimethylsulfoxide. More preferably, the co-solvent is ethanol.

The compositions of the present invention may optionally include one or more additives. Any additive that provides benefit to the intended use of the present invention is contemplated and includes additives known in the art and yet to be discovered. Exemplary additives include mineral salts, buffers, oncotic and osmotic agents, nutritive agents, flavorings, or palatability enhancers, or any other ingredient capable of augmenting the favorable characteristics of the compositions of the present invention including pharmaceutical stability, therapeutic efficacy and tolerance.

The compositions may also include additives for use in monitoring the delivery and potential absorption at a selected target of the composition including but not limited to colorings, dyes, or tracking agents. The monitoring agents such as dyes are used in conjunction with the composition to monitor the delivery of the composition to ensure optimum delivery and coverage of the selected target. The perfluorocarbon can be actively monitored with the use of conventional x-rays, cat-scans, MRI imaging, ultrasound and spectroscopy such as Raman spectroscopy. The monitoring can further be enhanced with the addition of certain additives or agents that allow a user to monitor and track the delivery and uptake of the composition at the desired target. Further, those skilled in the art will understand that many monitoring agents or additives could be used and will depend on the target site and treatment used.

II. METHODS

The present invention encompasses methods of targeting tissue cells in a subject harboring conditions or at risk for conditions that would benefit from gas-based and/or photodynamic therapy. The methods may be utilized to treat a subject harboring a condition that would benefit from gas-based and/or photodynamic therapy or that is at risk of developing a condition that would benefit from such therapy.

In one embodiment, the use of a perfluorocarbon emulsion, preferably perfluorooctyl bromide with demonstrable anti-stromal properties (i.e., perflubron), combined with a photosensitizer such as a near infrared dye (e.g., IRDye® 800CW, IRDye® 700DX, IRDye® 680LT, and IRDye® 680RD [LI-COR, Inc., Lincoln, NE]; preferably IRDye® 800CW or IRDye® 700DX) coupled to an antibody or other antigen-binding protein (e.g., panitumumab, bevacizumab, cetuximab), or small molecule such as a tyrosine kinase inhibitor (e.g., nintedanib) using oxygen gas therapy to treat tumors, microtumors, and/or other cancer forms with photodynamic therapy (PDT).

The inclusion of the anti-stromal perfluorocarbon with the anti-cancer drug mitigates cancer "rescue" by inhibiting stroma. Without residual stromal cells, remnant cancer cells cannot use those cells to recover and return. Furthermore, the inclusion of perfluorocarbon with the cancer drug-IR dye conjugate enables increased delivery of oxygen to the tumor to enhance PDT killing and also reduces hypoxia, which may reduce tumor aggressiveness.

A. Conditions Benefiting from Gas-Based Therapy

Conditions that would benefit from gas-based therapy, such as treatment with the fluorochemical composition, may include any condition or disease that is altered from normal physiological homeostasis. For instance, exemplary conditions that may benefit from gas-based therapy include, but are not limited to, sites of tissue injury, degeneration, neoplastic growth, dysplasia, hyperplasia, neoplasia, tumor formation, tumor growth, cancer, including but not limited to pancreas, ovarian, colon, liver, peritoneal, head and neck, lung, brain, glioblastoma, breast and sarcoma, tumor stroma, tumor nests, tumor associated fibroblasts, myofibroblasts, SMA positive cells, tumor associated macrophages, CD68, M1 macrophages, CD163 M2 macrophages, tumor stem cells, dendritic cells, lymphocytes, broncho-pulmonary dysplasia, osteoarthritis, and other conditions known in the art or yet to be discovered that may benefit from gas-based therapy. Further exemplary conditions may include, without limitation, acneiform eruptions, acute interstitial pneumonitis, autoinflammatory syndromes, arthritis, asthma, atherosclerosis, autoimmune diseases, Barrett's disease, bronchiolitis obliterans with organizing pneumonia, cancer chlorioretinal scarring, chronic blistering, chronic prostatitis, cirrhosis, colitis, connective tissue diseases, corneal scarring, Crohn's disease, dermal and subcutaneous growths, dermatitis, dermatomyositis, desquamative interstitial pneumonitis, diverticulitis, eosinophilic cutaneous conditions, epidermal cysts, epidermal neoplasms, epidermal nevi, fibromyalgia, glaucoma, glomerulonephritis, hepatitis, hypertrophic scarring, inflammatory bowel diseases, inflammatory demyelinating polyneuropathy, inflammatory myopathies, interstitial cystitis, interstitial lung disease, irritable bowel syndrome, ischemic heart disease, keloidal scarring, Lofgren syndrome, lupus, lupus erythematous, lymphocytic interstitial pneumonitis, macular degeneration, nephritis, nonspecific interstitial pneumonitis, osteoporosis, Parkinson's, pelvic adhesive disease, pelvic inflammatory disease, polymyalgia rheumatica, polymyositis, reperfusion injury, respiratory distress, respiratory bronchiolitis, retinal diseases, rheumatoid arthritis, sarcoidosis, skin grafts, spinal cord injuries, surgical scarring, systemic sclerosis, transplant rejection, ulcerative colitis, and vasculitis as well as others known in the art or yet to be discovered.

Also, methods of the invention may be utilized to treat a population of cells that would benefit from gas-based therapy. Such cells include those in a subject as well as those removed from a subject for therapeutic treatment, cultured cells, those used in gene-therapy practices, and any other cell that may benefit from gas-based therapy.

B. Methods of the Invention

Generally, methods of the present invention include administering to a subject a fluorochemical composition of the invention for use as a delivery mechanism to targeted cells and tissue. In one embodiment, the fluorochemical composition is a liquid. In another embodiment, the fluorochemical composition is an emulsion. In one embodiment, the fluorochemical composition is used to deliver to and enhance the retention of additional therapeutic agents, including gas-based therapeutics and bioactive agents, at targeted cells and tissues. In another embodiment, the fluorochemical composition is itself a therapeutic agent.

In one embodiment, the fluorochemical composition is delivered systemically. In another embodiment, the fluorochemical composition is delivered directly at the target site. In yet another embodiment, the fluorochemical composition is delivered via installation (instilling).

In certain embodiments, the fluorochemical composition is administered in combination with at least one additional therapeutic agent. In certain embodiments, the fluorochemical composition is administered sequential to an additional therapeutic agent. In other embodiments, the fluorochemical composition is administered prior to the administration of an additional therapeutic agent. In certain embodiments, the fluorochemical composition is administered prior to and after the administration of an additional therapeutic agent. In other certain embodiments, the fluorochemical composition is administered at the same time as at least one therapeutic agent. In certain embodiments, the fluorochemical composition may be administered without additional therapeutic agents. By way of example, the fluorochemical composition may be mixed with such gas before administration or administered in combination. For example, the gas may be added directly to the composition or provided to the subject through other means such as direct instillation of the gas in addition with a therapeutic agent (gemcitabine 10 mg/ml).

Methods of the invention include administering to a subject a fluorochemical composition as a delivery vehicle for other agents including agents used in imaging applications, bioactive agents, gas-based therapeutics, or combinations thereof. The properties and characteristics of a fluorochemical composition specifically target the composition and enhance the retention of the composition at target sites. Also, the properties and characteristics of a fluorochemical emulsion composition specifically aide in delivery of the composition (including the agent) to the target and enhance the retention of the composition at target sites. The activity of the fluorochemical acts with the agent causing a synergistic therapeutic effect. In one embodiment, the fluorochemical composition includes an emulsifying agent to create a fluorochemical emulsion composition. In another embodiment the fluorochemical composition is in a neat form without an emulsifying agent. In yet another embodiment, the fluorochemical composition is instilled to the target location. The fluorochemical composition may be used to target an agent to a location in a subject such that the retention time of the agent is improved compared to using the agent alone. The agent may be combined with the fluorochemical composition prior to administration. The fluorochemical composition and agent may work synergistically to benefit the subject.

Another embodiment includes administering to a subject a fluorochemical composition of the invention prior to a secondary therapy, and/or sensitizing the target area before the secondary therapy. Suitable secondary therapies include irradiation therapy, chemotherapy, combinations thereof and other therapies known in the art or yet to be discovered that would have enhanced efficacy following sensitization of the target area with compositions of the present invention. In one embodiment, the fluorochemical composition is used as a pre-treatment to the target area. Delivery of the fluorochemical composition as a pre-treatment enhances the gas delivery to the target area creating a better environment for enhancing the efficacy of the treatment therapeutic at the target area.

Methods of the invention include administering compositions of the present invention to a subject for the treatment of cancer. In one embodiment, the fluorochemical composition is aerosolized. In another embodiment, the fluorochemical composition is instilled. In one embodiment, the fluorochemical composition includes an emulsifying agent. In another embodiment, the fluorochemical composition is in a neat form without an emulsifying agent. For instance, the compositions are directly instilled or aerosolized at the site of tumor growth either alone or in combination with other therapeutics including gas-based therapeutics. Such methods are beneficial in the treatment of any and all cancer types known in the art or yet to be discovered. Exemplary cancer types to be treated include but are not limited to acute lymphoblastic leukemia, acute myeloid leukemia, adrenocortical carcinoma, anaplastic large cell lymphoma, appendix cancer, basal cell carcinoma, B cell cancer, bile duct cancer, bladder cancer, bone cancer (IGF-1 sensitive bone tumors), brain cancer, breast cancer, carcinoid tumor, cardiovascular cancer, cervical cancer, chronic lymphocytic leukemia, chronic myelogenous leukemia, colon cancer, colorectal cancer, epithelial carcinoma, epithelial cell-derived neoplasia, esophageal cancer, Ewing's sarcoma, gastric carcinoma, gastrointestinal cancer, gastrointestinal stromal tumors, glioblastoma multiforme, head and neck cancer, Hodgkin's lymphoma, kidney cancer, leukemia, lip cancer, liver cancer, lymphocytic leukemia, lymphoma, lung cancer, medulloblastoma, merkel cell carcinoma, melanoma, mouth cancer, multiple myeloma, Non-Hodgkin's lymphoma, non-small cell lung cancer, oropharyngeal cancer, osteosarcoma, ovarian cancer, pancreatic cancer, prostate cancer, rectal cancer, renal cell carcinoma, retinoblastoma, skin cancer (squamous cell cancer, basal cell cancer), small bowel cancer, small intestine cancer, soft tissue sarcoma, stomach cancer, and testicular cancer as well as other cancers known in the art.

C. Delivery Means and Routes

Methods of administration include any method known in the art or yet to be discovered. Exemplary administration methods include intravenous, intraocular, intratracheal, intratumoral, oral, rectal, topical, intramuscular, intraarterial, intrahepatic, intrathoracic, intrathecal, intracranial, intraperitoneal, intrapancreatic, intrapulmonary, gastrointestinal or subcutaneously.

The fluorochemical composition may be administered directly by instillation or as an aerosol. One skilled in the art will appreciate that the route of administration and method of administration depend upon the intended use of the compositions, the location of the target area, and the condition being treated in addition to other factors known in the art such as subject health, age, and physiological status. A skilled artisan will also recognize that methods using aerosol compositions may use a catheter placed through an appropriate scope and aerosolizing the composition using a nebulizer. Suitable nebulizers are known in the art. Exemplary nebulizers include but are not limited to the Aeroprobe™, Microsprayer™, Aerotech II™, Pari™ brand, or Aeroclipse™. Exemplary catheters and nebulizers include but are not limited to the Glo-Tip® Spray Catheter (Cook Medical, Bloomington, IN) and the PW-205V spray catheter (Olympus, Center Valley, PA). Alternatively, the compositions may be aerosolized using dry methods known in the art such as a dry powder inhaler or similar device.

In one embodiment, the fluorochemical-containing compositions (e.g., PIRC or other combination compositions containing perfluorocarbon or perfluorocarbon emulsion and near infrared labeled drug [e.g., IR800 labeled nintedanib] or targeting molecule (IR800 labeled cetuximab]) are nebulized to produce particles (aerosolized) with a diameter of $\leq 5.8$ μm, $\leq 5.7$ μm, $\leq 5.6$ μm, $\leq 5.5$ μm, $\leq 5.4$ μm, $\leq 5.3$ μm, $\leq 5.2$ μm, $\leq 5.1$ μm, $\leq 5.0$ μm, $\leq 4.9$ μm, $\leq 4.8$ μm, $\leq 4.7$ μm, $\leq 4.6$ μm, $\leq 4.5$ μm, $\leq 4.4$ μm, $\leq 4.3$ μm, $\leq 4.2$ μm, $\leq 4.1$ μm, or $\leq 4.0$ μm. In some embodiments $\geq 50\%$, $\geq 55\%$, $\geq 60\%$, $\geq 65\%$, $\geq 70\%$, $\geq 75\%$, $\geq 80\%$, $\geq 85\%$, $\geq 90\%$, or $\geq 95\%$ of the aerosol particles have a diameter $\leq 5.8$ μm.

Fluorochemical compositions of the invention are typically administered to a subject in an amount sufficient to provide a benefit to the target microenvironment of the subject. This amount is defined as a "therapeutically effective amount." The fluorochemical can be administered at ambient (temperature, pressure, etc.), conditions, below ambient conditions, above ambient conditions. Further the fluorochemical can be administered with bioactive agents at, below, or above ambient conditions. The therapeutically effective amount will be determined by the efficacy or potency of the particular composition, the duration or frequency of administration, and the size and condition of the subject, including that subject's particular treatment response. Additionally, the route of administration should be considered when determining the therapeutically effective amount. It is anticipated that the therapeutically effective amount of a fluorochemical composition of the invention will range from about 0.1 ml/kg to about 35 ml/kg. Depending on the target area and desired therapeutic agent used in conjunction (of in certain instances no additional therapeutic agent will be used) with the fluorochemical composition the amount of fluorochemical can include 0.01%, 1%, 5%, 10%, 15%, 20%, 25%, 30%, 35%, 40%, 45%, 50%, 55%, 60%, 65%, 70%, 75%, 80%, 85%, 90%, 95%, 99%, or 100% of the total therapeutic composition. In determining the therapeutically effective amounts, one skilled in the art will also consider the existence, nature, and extent of any adverse effects that accompany the administration of a particular compound in a particular subject.

III. KITS

The present invention provides articles of manufacture and kits containing materials useful for treating the conditions described herein. The article of manufacture may include a container of a compound as described herein with a label. Suitable containers include, for example, bottles, vials, and test tubes. The containers may be formed from a variety of materials such as glass or plastic. The container holds a composition having an active agent which is effective for treating, for example, conditions that benefit from gas-based therapy. The active agent is at least one fluorochemical composition of the invention and may further include additional fluorochemicals or bioactive agents known in the art for treating the specific condition. The label on the container may indicate that the composition is useful for treating specific conditions and may also indicate directions for administration.

IV. METHODS OF DETECTION AND TREATMENT

In accordance with the present invention, compositions and methods for the imaging and/or pre-treatment of lymphatic channels and lymph nodes prior to surgical resection are provided. In other embodiments, the method is used to image and/or treat non-cancer conditions, such as inter alia interstitial pulmonary fibrosis, atherosclerosis, and other fibrotic conditions. In other embodiments, the invention provides theranostic methods of detecting and treating cancer, pre-cancerous tissue, dysplasias, such as focal cortical dysplasia, colon dysplasia, Barrett's esophagus with dysplasia and without dysplasia. By theranostic, the method enables concurrent or sequential identification of cells or tissue of interest and the treatment or killing of said cells or tissue.

In one aspect, a therapeutic composition that comprises (i) a fluorochemical emulsion (e.g., perflubron) and (ii) a biological molecule complexed with (iii) a label is administered to a subject, and a laser or other form of electromagnetic radiation (EMR) is applied to the subject in a manner that excites the label. In some embodiments, the fluorochemical emulsion is charged with $O_2$. Without wishing to be bound by theory, the biological molecule serves to home-in on and bind to a target, thereby labeling the target molecule or cell that expresses the target molecule. The label is subsequently excited by the applied electromagnetic radiation and emits EMR of a wavelength that generates toxic reactive oxygen species around and within the target cell. This is known as photo-dynamic therapy (PDT). The oxygen charged fluorocarbon emulsion delivers an abundant supply of oxygen to enable the persistence of the reactive oxygen species sufficient to destroy the labeled cell and proximal cells, thereby rendering PDT much more effective.

Alternatively, the composition containing the fluorochemical emulsion (e.g., perflubron) and biological molecule complexed with a label is administered as a method of detecting target-specific cells in a subject. The laser or other light of a particular wavelength or range of wavelengths is shone onto the suspect tissue of the subject, and light emitted by the excited label returning to ground state is detected.

Thus, in one embodiment, the $O_2$-charged fluorocarbon emulsion plus labeled target-binding moiety composition ("$O_2$*") is delivered to a tissue or organ suspected of harboring a cancer cell, neoplastic, dysplastic or fibrotic tissue. The $O_2$* composition may be delivered to the target tissue by one or more of several routes. In one embodiment, the $O_2$* composition is delivered as an aerosol via an aerosolizing device, including for example an inhaler, a nebulizer, a small volume nebulizer, a pressurized metered-dose inhaler, a dry powder inhaler, an aerosol generator, and the like. In another embodiment, the $O_2$* composition is administered via pressurized intraperitoneal aerosol therapy, such as pressurized intraperitoneal aerosol chemotherapy (PIPAC), or other high pressure aerosolizing means. In other embodiments, the $O_2$* composition is delivered orally, intravenously, subcutaneously, or via installation into a cavity, such as intraperitoneal, intrabladder (intravesical), intravitreal, intraarticular, and the like. In one embodiment, a stent may be charged with the $O_2$* composition and delivered intravascularly or intralymphatically. In another embodiments, the $O_2$* composition is delivered via intra-arterial needle-free injection.

In one embodiment, the biological molecule that the label is affixed is an antigen-binding protein, such as an antibody, antibody fragment (e.g., Fab), soluble receptor, receptor fusion protein, receptor-Fc-fusion protein or trap molecule, and the like. For example, the biological molecule can be a monoclonal antibody that specifically binds a tumor antigen, an extra-cellular matrix protein, a stroma cell-specific antigen, or a fibroblast-specific antigen. Non-limiting examples of useful antibodies include anti-EGF receptor antibodies (e.g., cetuximab) for cancer, and anti-LOXL2 (e.g., simtuzumab) for fibrosis. (LOXL is involved in the cross-linking of collagen and elastin.) Examples of Fc-fusion proteins include the VEGF antagonist aflibercept, the inter-leukin-1 antagonist rilonacept and the TNF antagonist etanercept.

In some embodiments, the biological molecule comprises a soluble receptor fragment or a ligand that binds to a cell surface receptor. For example, the biological molecule may comprise the Arg-Gly-Asp tripeptide motif (RGD) of fibronectin that binds integrin. A labeled RGD-containing polypeptide will bind those cells that express integrins. Integrins are transmembrane receptors involved in cell-cell and cell-extracellular matrix (ECM) interactions. Integrins mediate fibroblast to ECM interaction and are important in tumor stromal cell integrity. Thus, those molecules having an RGD motif bind to cancer cells, neovasculature, peritumoral fibroblasts and macrophages, and other cancer stromal cells (i.e., fibroblast cells), making them an important tumor targeting moiety.

In some embodiments, the biological molecule is a small molecule that interacts with biological systems. For example, tyrosine kinase inhibitors are biological molecules since they bind to cell signaling molecules in a cell, and affect cell signaling and cell proliferation. Useful tyrosine kinase inhibitors that can be labeled and used in the $O_2$* composition include inter alia afatinib, axitinib, bafetinib, bosutinib, cediranib (Recentin), crizotinib, dasatinib (Sprycel), erlotinib hydrochloride (Tarceva), gefitinib (Iressa), imatinib (Gleevec, Glivec), lapatinib (Tykerb/Tyverb), lestaurtinib, neratinib, nilotinib (Tasigna), nintedanib, ponatinib, quizartinib, regorafenib, ruxolitinib, sunitibin (Sutent), tofacitinib, vandetanib (Zactima), N-acetylcysteine, and vatalanib.

The biological molecule of the $O_2$* composition comprises a label. In some embodiments, the label is covalently linked to the biological molecule. In some embodiments, the label is a fluorescent molecule that is excited by EMR at a first wavelength, and emits EMR at a second wavelength. Useful fluorescent labels include quantum dots, lanthanide series chelates (e.g., terbium, europium), fluorescein derivatives, rhodamine derivatives, coumarin derivatives, cyanine derivatives, near infra-red probes, including for example IRDye® 800CW, IRDye® 700DX, IRDye® 680LT, and IRDye® 680RD (LI-COR, Inc., Lincoln, NE).

A laser that emits EMR at the excitation wavelength of the dye is selected and applied to the target area. The dye absorbs the light, and emits light of a lower wavelength. Thus, in some embodiments where the biological molecule is labeled with IRDye® 700DX or IRDye® 800CW, the laser emits light in the near IR (i.e., about 700 nm or 800 nm) to excite the labeled target and create cell-damaging emission light.

A. Photoimmunotherapy (PIT) Compositions

In one embodiment, a method of killing or removing a tumor containing stromal and cancer cells is provided. The inventor has made the surprising discovery that combining a fluorescently labeled anti-cancer drug with a perfluorocarbon emulsion significantly enhances the photodynamic tumor-killing power of the labeled drug and improves the durability of the cancer killing effect. While not wishing to be bound by theory, the inclusion of the perfluorocarbon emulsion, preferably a bromine-containing perfluorocarbon emulsion such as perflubron, (1) enhances the formation of reactive oxygen species by providing additional oxygen, (2) improves the antibody binding to its cognate target on the cell, and/or (3) enhances the tumor to background ratio of fluorescent signal and overall intensity. In some embodiments, the combination is administered to the patient in need, or to the tumor or tumor cells via spray catheter, an inhaler, or the like.

In some embodiments, the labeled drug is monoclonal antibody conjugated with a near infrared dye, such as IR700 (mAb-IR700). It is generally known in the art that mAb-IR700 is an effective anti-cancer medicament when used in photoimmunotherapy (PIT). Mitsunaga et al., for example describes the effectiveness of trastuzumab-IR700 and panitumumab-IR700 PIT in killing HER2-expressing 3T3 cells. Here, the combination of the mAb-IR700 with perflubron emulsion significantly improves the PIT killing effect of mAb-IR700 by ≥10%, ≥15%, ≥20%, ≥25%, ≥30%, ≥35%, ≥40%, ≥45%, ≥50%, ≥55%, ≥60%, ≥65%, ≥70%, ≥75%, ≥80%, ≥85%, ≥90%, ≥95%, ≥100%, ≥150%, ≥200%, ≥4-fold, ≥5-fold, ≥6-fold, ≥7-fold, ≥8-fold, ≥9-fold, ≥10-fold, ≥15-fold, ≥20-fold, ≥25-fold, ≥50-fold, ≥75-fold, or ≥100-fold over the mAb-IR700 in the absence of perflubron emulsion. In some embodiments, the labeled anti-cancer drug is cetuximab-IRDye®800CW. Here, when combined with the perfluorocarbon, the 800 nm photosensitizer is effective in killing cancer cells, a property heretofore not observed for IR800.

In some embodiments, the near infrared fluorescent label has an absorbance maximum at any wavelength along the near infrared section of the EMR spectrum. In some embodiments, near infrared (NIR) includes EMR with a wavelength of about 700 nm to about 1400 nm. While IR700 dyes have been shown to have some efficacy in PIT cancer cell killing, IR800 has heretofore been not shown to be effective in PIT. The inventor has discovered that the combination of mAb-IR800 with a perfluorocarbon emulsion is effective as a PIT composition to kill tumors. This provides several advantages of traditional IR700 PIT, one of which is the deeper tissue penetration of 800 nm light into tissues and the concomitant improved tumor background ratio (TBR), another is the increased availability in medical facilities and lower cost of 800 nm lasers and cameras over 700 nm systems.

While not wishing to be bound by theory, the improved effectiveness of the perfluorocarbon plus mAb-IR700 or mAb-IR800 composition over the mAb-IR700 or mAb-IR800 composition without the perfluorocarbon, may be due in part inter alia to (1) the improved oxygen delivery by the perfluorocarbon to the site of PDT, thereby enhancing sustained generation of reactive oxygen species, and/or (2) the killing effect of perfluorocarbon formulations on tumor stromal cells and other peri-tumoral fibroblasts and macrophages.

In one embodiment, a composition comprising a biological molecule-near infrared fluorophore conjugate (NIR-C) and a perfluorocarbon emulsion is provided. In one embodiment, the biological molecule is an antibody or an antibody fragment, such as a Fab. In one embodiment, the biological molecule is a monovalent monospecific antibody or fragment thereof. In another embodiment, the biological molecule is a bivalent monospecific antibody or fragment thereof. In another embodiment, the biological molecule is a bivalent bispecific antibody or fragment thereof, or other multispecific antigen-binding protein. In another embodiment, the biological molecule is an immunoadhesin (Ashkenazi and Chamow, Methods, 8(2): 104-115, 1995) or other receptor Fc-fusion protein or trap molecule.

In a specific embodiment, the antibody is cetuximab or an antibody-drug conjugate thereof. In a more specific embodiment, the NIR-C is cetuximab-IRDye® 700DX. In another specific embodiment, the NIR-C is cetuximab-IRDye® 800CW.

The perfluorocarbon and NIR-C are combined in various proportions according to the particular application. In one embodiment, the weight-to-weight ratio of perfluorocarbon to NIR-C (perfluorocarbon/NIR-C) is about 0.5-2000, 1-1000, 10-500, 50-500, 200-700, 10, 20, 30, 40, 50, 60, 70, 80, 90, 100, 200, 300, 400, 500, 600, 700, 800, 900, 1000, 1200, 1400, 1600, 1800, 2000, or >2000. Preferred weight-to-weight ratios of perfluorocarbon to NIR-C (perfluorocarbon/NIR-C) include 100, 150, 200, 250, 300, 350, 400, 450, 500, 550, and 600. In a preferred embodiment, the weight-to-weight ratio of perfluorocarbon to NIR-C (perfluorocarbon/NIR-C) is 300±45 or 150±23.

In some embodiments, the perfluorocarbon is formulated in a first part and the NIR-C is formulated in a second part, and then the first and second parts are combined to form the perfluorocarbon/NIR-C combination. In one embodiment, the perfluorocarbon-containing first part contains ≥10%, ≥20%, ≥30%, ≥40%, ≥50%, ≥60%, ≥70%, ≥80%, ≥90%, 100%, 50%-100%, 50%-90%, 50%-80%, 50%-70%, 40%, 45%, 50%, 55%, 60%, 65%, 70%, 75%, 80%, 85%, 90%, 95%, 96%, 97%, 98%, 99% or 100% perfluorocarbon.

In some embodiments, the perfluorocarbon-containing first part also contains an emulsifier, such as, e.g., egg yolk phospholipid and/or lecithin. In one embodiment, the perfluorocarbon-containing first part contains ≤1%, ≤2%, ≤3%, ≤4%, ≤5%, ≤6%, ≤7%, ≤8%, ≤9%, ≤10%, ≤15%, ≤20%, ≤25%, ≤30%, ≤35%, ≤40%, ≤45%, or ≤50% emulsifier. In a preferred embodiment, the perfluorocarbon-containing first part contains 60% perfluorocarbon and 40% emulsifier.

In some embodiments, the NIR-C-containing second part contains about 0.5-200 mg/mL, 1-100 mg/mL, 10-100 mg/mL, 20-200 mg/mL, 1 mg/mL, 2 mg/mL, 5 mg/mL, 10 mg/mL, 15 mg/mL, 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 110 mg/mL, 120 mg/mL, 130 mg/mL, 140 mg/mL, 150 mg/mL, 160 mg/mL, 170 mg/mL, 180 mg/mL, 190 mg/mL, 200 mg/mL, or 250 mg/mL NIR-C. A preferred NIR-C-containing part contains about 2 mg/mL NIR-C.

In some embodiments, the perfluorocarbon-containing part is combined with a diluent prior to or concomitantly with combining with the NIR-C-containing part. In one embodiment, the diluent is a buffered aqueous solution, such as phosphate-buffered saline (PBS). In one embodiment, the perfluorocarbon-containing part (perj) is combined with the diluent in a volume-to-volume ratio (perfdiluent) of 100:0, 95:5, 90:10, 80:20, 75:25, 70:30, 65:35, 60:40, 55:45, 50:50, 45:55, 40:60, 35:65, 30:70, 25:75, 20:80, 10:90, or 5:95 to form a diluted perfluorocarbon-containing part (dilperf).

In one embodiment, the subject diluted perfluorocarbon-containing part (dilperf) is combined with the NIR-C-containing part (nirc) in a volume-to-volume ratio (dilperf:nirc) of 95:5, 90:10, 80:20, 75:25, 70:30, 65:35, 60:40, 55:45, 50:50, 45:55, 40:60, 35:65, 30:70, 25:75, 20:80, 10:90, or 5:95 to form the perfluorocarbon-NIR-C combination PIRC). For the sake of clarity, a 50:50 dilperf:nirc ratio represents 25:25:50 perf:diluent:nirc. In a preferred embodiment, the perfluorocarbon-containing part is combined with diluent at a volume to volume ratio of 50:50, and the diluted perfluorocarbon containing part is then combined with the NIR-C-containing part at a volume to volume ratio of 50:50. Preferably a perfluorocarbon emulsion containing 60% (w/v) perfluorocarbon and 40% (w/v) emulsion is combined 50:50 with a diluent such as PBS, and then combined with an NIR-C containing about 2 mg/mL of the biological molecule, to form a combination (i.e., PIRC) containing 30% (w/v) perfluorocarbon, 20% (w/v) emulsion, 1 mg/mL biological molecule. A preferred biological molecule is an anti-cancer monoclonal antibody, such as cetuximab, linked to an IR700 or IR800 fluorophore.

B. Use of Photoimmunotherapy Compositions

In one embodiment, (1) the PIRC is administered to a patient (human subject or animal) intravenously, (2) the tumor is imaged, and (3) the tumor is biopsied, removed or otherwise disturbed. In one embodiment, the tumor is subjected to photodynamic therapy at or near the time of imaging and prior to disturbing the tumor. In one embodiment, the patient is subjected to further cancer treatment such as surgery, radiation therapy, and/or chemotherapy.

In one embodiment, the patient is administered a therapeutically effective amount of oxygen prior to imaging, PDT or otherwise disturbing the tumor. The amount of oxygen delivered to the patient is selected to optimize the amount of oxygen surrounding the tumor to enhance the sustained production of reactive oxygen species at the tumor site during and after photodynamic therapy. While not wishing to be bound by theory, sustained delivery of an amount of oxygen to a patient may over time lead to vasoconstriction and consequent reduction of oxygen to the tumor site. Therefore, the practitioner of ordinary skill in the art can adjust the amount and timing of oxygen delivery to the patient to deliver optimal amounts of oxygen to the tumor for sustained effective PDT.

In one embodiment, the patient is administered an amount of oxygen 2-5 minutes, 10 minutes, 9 minutes, 8 minutes, 7 minutes, 6 minutes, 5 minutes, 4 minutes, 3 minutes, 2 minutes, 1 minute, or less than 1 minute prior to delivery of the PDT light to the tumor. In one embodiment, the amount of oxygen delivered to the patient's lungs is >21 kPa, 25-101 kPa, 25 kPa, 30 kPa, 35 kPa, 40 kPa, 45 kPa, 50 kPa, 55 kPa, 60 kPa, 65 kPa, 70 kPa, 75 kPa, 80 kPa, 85 kPa, 90 kPa, 95 kPa, or 101 kPa.

In one embodiment, (1) the PIRC is administered to the patient a few minutes, less than about one hour, about 4 hours, about 6 hours, about 8 hours, about 16 hours, about 24 hours, about 32 hours, about 40 hours, about 48 hours, about 3 days, about 4 days, about 5 days, about 6 days, or about 7 days prior to (2) imaging or applying light for PDT prior to or concomitantly with biopsy or resection of the tumor. In one embodiment, the PDT light (e.g., laser or other light source tuned to the subject fluorophore) is administered to the tumor at a dose of 40-500 $J/cm^2$, ≥50 $J/cm^2$, 50-75 $J/cm^2$, 40-120 $J/cm^2$, 70-260 $J/cm^2$, 20 $J/cm^2$, 30 $J/cm^2$, 40 $J/cm^2$, 50 $J/cm^2$, 60 $J/cm^2$, 70 $J/cm^2$, 80 $J/cm^2$, 90 $J/cm^2$, 100 $J/cm^2$, 110 $J/cm^2$, 120 $J/cm^2$, 130 $J/cm^2$, 140 $J/cm^2$, 150 $J/cm^2$, 160 $J/cm^2$, 170 $J/cm^2$, 180 $J/cm^2$, 190 $J/cm^2$, 200 $J/cm^2$, 220 $J/cm^2$, 240 $J/cm^2$, 260 $J/cm^2$, 280 $J/cm^2$, 300 $J/cm^2$, 350 $J/cm^2$, 400 $J/cm^2$, 450 $J/cm^2$, or 500 $J/cm^2$.

In one embodiment, the therapeutic light is delivered inter alia by a laser, a non-laser light source, an over-the-shoulder light source, or a fiber optic line positioned in, at or near the tumor.

In another embodiment, (1) the PIRC is administered peritumorally or intratumorally, (2) the tumor is imaged, and (3) the tumor is biopsied, removed or otherwise disturbed. In one embodiment, the tumor is subjected to photodynamic therapy at or near the time of imaging and prior to disturbing the tumor. In one embodiment, the patient is subjected to further cancer treatment such as surgery, radiation therapy, and/or chemotherapy. Here, a therapeutically effective amount of oxygen is delivered to the tumor or combined with the PIRC prior to or during intratumoral, intravenous, or peritumoral administration to promote ROS formation during PDT.

In one embodiment, after the PIRC is administered around the tumor, the PIRC is allowed to diffuse into the lymph vessels and sentinel lymph node. The lymphatic system proximal to the tumor is then mapped by following the fluorescent signal. The lymph channel and nodes are then subjected to PDT before to, during, and/or after the tumor is biopsied, excised, or otherwise disturbed. Administration of light to the lymph system and other areas proximal to the tumor post-disturbance is called "surgical sterilization" since it kills tumor cells that are already present but not able to be visualized by current imaging techniques but nonetheless present, or cells that moved from the tumor into the surrounding tissues during disturbance (tumor cell spread) and proximal microtumors.

In some embodiments, after the surgeon removes tumor and lymph nodes, intraoperative x-ray, fluoroscopy, CT, MRI, or other imaging methods can be used to identify any perfluorocarbon, which indicates the presence of residual tumor cells, to enable the surgeon to verify that all lymphatic channels and lymph nodes have been removed. Surgical oncologists often try to blindly remove every node possible during surgery, but this can be challenging.

Non-limiting examples of cancer/tumors that can be treated by both intravenous and peritumoral/intratumoral PIRC administration include inter alia melanomas, breast cancers, head and neck cancers, pancreas cancers, and lung cancers.

In another embodiment where the tumor is mucosal, cutaneous, subcutaneous, or near the surface of the skin, (1) the PIRC or perfluorocarbon formulation is applied to the surface of the skin, and (2) the tumor is imaged with probe confocal laser endomicroscopy confocal microscopy prior to biopsy, excision, or other disturbance of the tumor and subsequent surgical sterilization.

C. Improved Visualization of Mucosa

In one embodiment, perfluorocarbon or perfluorocarbon emulsion (e.g., perflubron) is washed over the surface of the skin or mucosa to facilitate removal of mucus and to further smooth the surface of the mucosa to enable better contact and smoother laser delivery and retrieval of Raman spectra wavelengths for cancer detection and cancer cell ablation. In a specific embodiment, the mucosal surface is of the esophagus and the perfluorocarbon is pushed down, where it removes the mucus enables the endoscopist to more clearly visualize color changes in the lower esophagus associated with Barrett's esophagus. The color change is associated with dysplasia in the layer. In one embodiment, the perfluorocarbon increases the sensitivity and specificity of detection of dysplasia by ≥50%, ≥60%, ≥70%, ≥80%, ≥90%, or ≥100% over traditional methods, such as the administration of N-acetylcysteine (NAC) alone as a surface preparation. In one embodiment, the perfluorocarbon is administered along with NAC.

D. Pretreatment of Lymphatic Channels, Lymph Nodes, and Other Suspect Tissue Prior to Resection The manipulation of tissue containing or suspected of containing cancer or pre-cancer cells increases the risk of mobilizing transformed cells that may colonize a distal area. Here, a suspect tissue is injected or otherwise contacted with the $O_2$* composition and subjected to laser treatment. For example, in one embodiment, a patient with a low rectal cancer has his tumor injected (or peritumoral application) with a composition comprising oxygenated perflubron and cetuximab labeled with IRDye® 700DX. Then, using robotic surgery (e.g., Da Vinci Robotic surgery, Intuitive Surgical, Inc., Sunnyvale, CA), the intraperitioneal space is entered with instruments and the tumor area is treated with the appropriate laser (e.g., i.e., 700 nm or 800 nm excitation) prior to surgical manipulation to reduce recurrent metastasis in the lymph node basin.

Likewise, in one embodiment, in the case of head and neck cancer, the subject area is injected (subcutaneous, intravenous, etc.) with the $O_2$* composition containing the appropriate labeled biological molecule. The area may then be imaged or treated with a laser or other PDT device prior to manipulation of the suspect tissue by surgical instruments.

In one embodiment, a PIRC is administered to the patient (e.g., intravenous or intra/peritumoral). In one embodiment, a fluorescent positive signal obtained by using a known malignant cell target, e.g., cetuximab or panitumumab, enables the diagnosis of cancer, and then, if properties present, to allow the generation of sufficient and effective reactive oxygen species at PDT.

Thus interfacing the specific monoclonal antibody or TKI for already approved anticancer drugs and administered by approved routes e.g. intravenous, subcutaneous or oral (but also intratumoral and other pathways) then use PDT prior to biopsy. Thus if cells or collection of cells known to be released as tumor exosomes containing stromal elements escape at or shortly after biopsy but first pre-treated with PDT, there will be an unsuccessful metastasis Following PIRC (e.g., perflubron+cetuximab-IRDye®-800CW or perflubron+panitumumab-IRDye®-800CW) the primary, lymphatic channels and lymph nodes wherever possible will be treated prior to resection and then once removed the area will be "sterilized" by PDT. Lymphatic channels, which are normally difficult to identify, can be identified with near infrared, fluoroscopy, X-ray, CT, Raman spectroscopy, and MRI by using a perfluorocarbon, preferably a brominated perfluorocarbon and concomitant or subsequent treatment with PDT before removal.

E. Interstitial Pulmonary Fibrosis (IPF)

IPF may be imaged and/or treated as described above. In one embodiment, subject lungs are aerosolized daily with 10 ml of an $O_2$* composition using a device such as e.g., an Aeroneb® Pro (Aerogen, Inc., Deerfield, IL). Here, the $O_2$* composition contains a monoclonal antibody (e.g., simtuzumab), a small molecule (e.g., a TKI such as nintedanib), other anti-fibroblast drugs such as pirfenidone, a ligand-containing polypeptide (e.g., an RGD-containing peptide or other integrin-binding moiety), or a like biological molecule that targets myofibroblasts—attached with a label (e.g., IRDye® 700DX or IRDye® 800CW). The tissue is then imaged, or lasered with a 700 nm or 800 nm laser as in PDT. Here, the oxygen charged fluorochemical provides an oxygen-rich microenvironment to support extensive ROS generation and concomitant cell killing.

In one embodiment, imaging can be performed with CT, MM (which can see perfluorocarbon emulsion), near infrared detection (e.g., using Multispectral optoacoustic imaging [MSOT] or the like) and/or Raman spectroscopy. Laser treatment can be performed via bronchoscopy for example once per week for 3 weeks by using an endoscopic device capable of delivering near infrared wavelength to stimulate for photodynamic killing of the target cells (e.g., cancer cells, tumor associated macrophages and tumor associated myofibroblasts).

F. Melanoma

Melanoma or other skin or subcutaneous cancer may be imaged and/or treated similarly. Using a needle free injection device, an $O_2$* composition can be delivered to the oral cavity, head or neck, or trunk, or extremity. Here, the $O_2$* composition contains a monoclonal antibody (e.g., simtuzumab, bevasizumab, cetuximab, panitumumab), a small molecule (e.g., a TKI such as nintedanib), a ligand-containing polypeptide (e.g., an RGD-containing peptide or other integrin-binding moiety), or a like biological molecule that targets the tumor cells or its supporting stroma— attached with a label (e.g., IRDye® 700DX or IRDye® 800CW). The tissue is then imaged, or lasered with a 700 nm or 800 nm laser as in PDT. Here, the oxygen charged fluorochemical provides an oxygen-rich microenvironment to enhance diagnostic imaging and support extensive ROS generation and concomitant cell killing. In some embodiments, diagnostic imaging for melanoma includes Raman spectroscopy, which can be used as a screen for melanoma when coupled with probe confocal laser endomicroscopy for "bloodless diagnosis".

In another embodiment, the melanoma is injected peritumorally with the $O_2$* composition containing a monoclonal antibody (e.g., simtuzumab), a small molecule (e.g., a TKI such as nintedanib), a ligand-containing polypeptide (e.g., an RGD-containing peptide or other integrin-binding moiety), or a like biological molecule that targets the tumor cells or its supporting stroma—attached with a label (e.g., IRDye® 700DX or IRDye® 800CW). The tissue is then imaged using MSOT or other NIR unit. The tissue is then lasered using a percutaneous unit or laser fibers emitting EMR at 700 nm or 800 nm prior to tissue removal. This procedure is expected to reduce or eliminate metastatic melanoma in the lymphatic channels (i.e., "melanoma in transition").

G. Hepatic Fibrosis

In other embodiments, the method applies to the imaging and treatment of other fibroses, such as nonalcoholic fatty liver disease (Nonalcoholic Steatohepatitis or NASH), cirrhosis, or other hepatic fibroses, and bile duct fibrosis such as primary sclerosing cholangitis. Here, the $O_2$* composition is delivered via the portal vein, intravenous or intrahepatic. Photodynamic therapy can be delivered in e.g., 3 to 5 days H. IR Guided Laser Prior to Biopsy In one embodiment, the method is incorporated in the biopsy step. Here, a patient with a mass (e.g., a mass in the neck) is injected minutes to days prior to procedure with an $O_2$* composition (oxygenated fluorocarbon emulsion plus labeled biological molecule specific for the target cancer). The interventional radiologist (IR) advances the biopsy needle toward the mass, and as the needle approaches or contacts the surface of the suspect mass a laser that is incorporated into the needle device is fired and kills the cells about to be biopsied. This procedure is expected to help ensure that any cancer cells that may be ejected by insertion of the needle are dead. A similar procedure can be employed intra-abdominally for example, or other similar situations.

I. Coronary Artery Blockage

In one embodiment, a patient with severe multiple coronary artery blockages that is not amenable to insertion sequential stents. Here, the patient is administered the $O_2$* composition, and subsequently lasered (e.g., 3 days later) by heart catheter. Dissolvable stents may be used.

J. Imaging Methods and Scope-Based Treatment

Perflubron (PFOB) and perflubron emulsion (PFCE) and their gas-based properties enable improved imaging and screening of a variety of areas for cancer within the human or animal subject. Non-limiting examples of newer imaging modalities that can be enhanced with perflubron or perflubron emulsion include Optical Coherence Topography (OCT), Narrow Band Imaging (NBI), Raman spectroscopy such as Surface-Enhanced Raman Spectral Scattering (SRS). See Podoleanu, "Optical coherence tomography," The British Journal of Radiology, 78(935), 2014; Hamamoto et al., "Usefulness of narrow-band imaging endoscopy for diagnosis of Barrett's esophagus," Journal of Gastroenterology, January 2004, Volume 39, Issue 1, pp 14-20; and Qian et al., "In vivo tumor targeting and spectroscopic detection with surface-enhanced Raman nanoparticle tags," Nature Biotechnology 26, 83-90 (2008), for describing OCT, NBI and Raman spectroscopy or SRS, respectively.

Perflubron or perflubron emulsion and other perfluorocarbons and emulsions are contemplated to be superior tumor imaging agents than those agents that are currently in use. The perflurocarbons or their emulsions also enable the viewing of the effects of treatment to enable improved outcomes for patients. In some embodiments, the visualization of tumors or other transformed or pre-cancerous cells with PFOB/PFCE by OCT and NBI is followed by gas-based treatment such as photodynamic therapy (PDT) and subsequent resection of the tumor or other transformed cells. Here, the perfluorocarbon preferentially binds to and (1) enables the identification of fibroblasts and macrophages, which flags the location of the cancer, and (2) enables the inhibition or killing of the fibroblasts and macrophages (as well as the cancer cells) after PDT.

In some embodiments, Raman spectroscopy or SRS is used to clearly and rapidly identify the carbon-fluorine (C—F) bonds. C—F bonds have a Raman emission signature that indicates the location of the perfluorocarbon molecules. In some embodiments, a colonoscope or other endoscope such as bronchoscope, cystoscope and upper gastrointestinal endoscope incorporates Raman spectroscopy or SRS to identify the perflubron or perflubron emulsion to enable gas based therapy. In some embodiments, commercial instruments such as the Verisante AURA™ (Veritante Technology, Inc., Richmond, BC) or i-RAMAN® (B&W Tek, Newark, DE) handheld Raman spectroscopy devices or other scopes are used.

In some embodiments, a PFOB/PFCE is delivered to a patient, e.g., per os for the GI tract, or instilled or aerosolized into, e.g., the GI tract, lungs, bladder, or peritoneal cavity. The target is then probed (e.g., 0.05-24 hours later) with a Raman spectroscopy or SRS probe to identify possible cancer cells.

Perflubron or perflubron emulsion targets and perfuses fibroblasts and macrophages, and concentrates near tumors. In some embodiments, a Raman spectroscopy or SRS probe is used to "excite" the C—F bonds of the perfluorocarbon molecules with a laser and generate a characteristic signal. C—F bonds are generally not found in nature, therefore when the probe identifies the C—F signal it identifies the location of the perflubron or perflubron emulsion product. When the C—F bond is detected, then the concomitantly added fluorescent dye such as ICG or IRDye combinations is delivered. A second imaging modality such as probe confocal laser endomicroscopy (pCLE) is then used to confirm that the signal is generated from a cancer as opposed to an infection that recruits macrophages and generates a non-cancer C—F signal. Regardless of the potential to initially detect non-cancer signals, the sensitivity of Raman spectroscopy and the SRS will enable fewer cancer lesions to be missed by the physician whether on skin or intraluminal (e.g. oral cavity, esophagus, stomach, colon, bladder or peritoneum).

One of the major problems currently associated with image guided surgery is the undefined edges of a tumor ("fuzzy" outline of the tumor) making clean resection of the tumor difficult for the surgeon. Raman spectroscopy can be used to identify C—F bonds after IRDye administration to visualize the well-marked edges of the tumor to enable more complete removal of the tumor.

In some embodiments, once cancer or tissues or cells-of-interest are identified by non-invasive means, gas based treatment of the lesion prior to biopsy can be performed and the lesion removed. In some embodiments, if cancer is suspected as negative pCLE, then PDT and biopsy can be subsequently performed.

V. DEFINITIONS

As used herein, "administering" is used in its broadest sense to mean contacting a subject with a composition of the invention.

As used herein, the phrase "metabolic inhibitor" is used in its broadest sense to refer to any bioactive molecule capable of altering at least one metabolic process of a cell. Any metabolic process affecting molecule known in the art or yet to be discovered is contemplated herein. Exemplary metabolic processes include, without limitation, nucleic acid synthesis, amino acid metabolism, protein synthesis, lipid synthesis, glycolysis, mitochondrial metabolism, TCA cycle, fatty acid metabolism, NAD metabolism, phosphoinositide 3-kinase signal transduction, and any other metabolic process relied upon by cancer or pre-cancerous cells.

As used herein, "subject" refers to a living organism having a central nervous system. In particular, subjects include, but are not limited to, human subjects or patients and companion animals. Exemplary companion animals may include domesticated mammals (e.g., dogs, cats, horses), mammals with significant commercial value (e.g., dairy cows, beef cattle, sporting animals), mammals with significant scientific values (e.g., captive or free specimens of endangered species), or mammals which otherwise have value. Suitable subjects also include: mice, rats, dogs, cats, ungulates such as cattle, swine, sheep, horses, and goats, lagomorphs such as rabbits and hares, other rodents, and primates such as monkeys, chimps, and apes. In some embodiments, subjects may be diagnosed with a fibroblastic condition, may be at risk for a fibroblastic condition, or may be experiencing a fibroblastic condition. Subjects may be of any age including new born, adolescence, adult, middle age, or elderly.

The terms "target" and "target site" refer to any site that would benefit from receiving the compositions of the present invention. The terms include cells, tissues, aberrant growths, tumors, cancerous lesions, sites of injury, and other sites that may benefit from the compositions of the invention.

The phrase "therapeutic agent" is used herein to refer to any agent that may provide a benefit to a target microenvironment. It is also used to refer to bioactive agents and gaseous substances.

The phrase "therapeutically effective amount" is used herein to mean an amount sufficient to increase to some beneficial degree, preferably to increase by at least about 1 to 100 percent, more preferably by at least about 5 to 95 percent, and more preferably by at least 8 percent or higher, healing or cancer cell death as compared to untreated controls. An "effective amount" is a pharmaceutically-effective amount that is intended to qualify the amount of an agent or compound, that when administered to a subject, will achieve the goal of healing an injury site, increasing cancer cell death, or otherwise benefiting the recipient environment.

The phrase "fluorocarbons" is used herein can mean perflubron, perfluorocarbon (PFC) in neat form or as an emulsion (PFCE), or a fluorochemical.

As various changes could be made in the above compositions and methods without departing from the scope of the invention, it is intended that all matter contained in the above description and in the Examples given below, shall be interpreted as illustrative and not in a limiting sense.

EXAMPLES

The following examples are simply intended to further illustrate and explain the present invention. The invention, therefore, should not be limited to any of the details in these examples.

Example 1. Treatment of Cancer Cells

The ability of fluorocarbons to dissolve and carry large amounts of gaseous substances makes them a novel anti-cancer therapeutic that may alter the cancer-promoting environment to be less habitable for pre-cancer and cancer cells. To analyze the effectiveness of the combination of fluorocarbons and gaseous substances as an anti-cancer therapeutic, the growth of cancer cells was measured in the presence of fluorocarbon with normal environment (Normoxia) or fluorocarbon with carbon dioxide (Hypoxia).

In particular, two human pancreatic cancer cell lines (Pan02 and Capan2) and one immortalized human pancreatic stellate cell line were cultured by methods known in the art. Briefly, cells were plated to 30% confluence and then perflubron/Egg Yolk Phospholipid emulsion (5.8 mg Perflubron/mL) was added to culture wells in triplicate at dilutions of 1:10, 1:20, 1:40, 1:80, 1:160, 1:320, 1:640, and 1:1280. Following administration of perflubron, samples were either maintained in normoxia conditions (i.e. room air) or hypoxia conditions (i.e. 1% $O_2$). The metabolic activity was assayed using Almar Blue staining. The fluorocarbon plus carbon dioxide treatment reduced the metabolic activity of immortalized human pancreatic stellate cells as well as pancreatic cancer cells. These results show that fluorocarbon, alone, inhibits cancer cell metabolic activity. Further, these results show that fluorocarbon in combination with gas has greater efficacy at inhibiting cancer cell metabolic activity specifically, in human pancreatic stellate and Pan02 cancer cells greater efficacy of inhibition including metabolic activity was shown in hypoxia, while in Capan2 cancer cells more inhibition was shown in normoxia.

Example 2. Cancer Therapy

A subject with a cancerous mass will undergo a pre-treatment CT/PET scan with fludeoxyglucose (FDG) and fluoromisonidazole (FMISO), a tumor hypoxia agent, to establish a baseline. This scan will also identify the volume and location of the hypoxic areas of the cancer mass. Next, at least one needle catheter will be inserted into the tumor and intratumoral pressure will be obtained. If a high intratumoral pressure is observed, a slow instillation of collagenase over 10 minutes could be considered to reduce the pressure (e.g. 30-40%). At this time, intravenous administration of a perfluorocarbon emulsion, chemortherapeutics, radiation agents, or a combination thereof, could be performed to utilize tumor vessels. Since the tumor pressure is lowered by the collagenase, this may enable a higher percent of drug delivery into the tumor.

Once a maximal amount of the intravenous medicine is in the tumor (e.g. ~4 hours), a slow injection with or without a convection pump of the perfluorocarbon emulsion alone or in combination with additional cancer therapeutics will be injected into the tumor up to a tumor volume amount. Other cancer therapeutics may include chemotherapeutics, radiation (i.e. Rhenium 186), metabolic inhibitors (i.e. 2-Deoxy D Glucose (2DG) and glutaminatic drugs), and combinations thereof. Since the perfluorocarbon emulsion can be visualized in real time by ultrasound, the activity of the injection collapsing the tumor vasculature trapping the perfluorocarbon and chemotherapeutic agents can be monitored. Following the injection of perfluorocarbon, 100% oxygen will be administered systemically or locally, such as intratumorally. The oxygen will be used to enhance chemotherapeutic agents or radiation agents that require oxygen to be effective over the next 2 hours. External beam radiation could also be used at this point. A PET scan or Near Infrared Imaging scan two hours later will be done to examine the hypoxia status. Then, 100% $CO_2$ gas will be add for 2 hours at a rate up to tumor volume per minute. A capnograph every 10 minutes up to 2 hrs at a rate to saturate the tumor volume per minute will be used to determine the subject's $CO_2$ levels. An ABG every 30 minutes will be performed to follow $CO_2$ until the 2 hour $CO_2$ gas treatment is complete. A CT/PET scan with FDG will be done within 30 minutes after $CO_2$ administration is complete and then again at 4 weeks post-treatment.

Example 3. Metastatic Carcinoma with Ascites

A patient with metastatic colon cancer exhibiting peritoneal studding and greater than 1 liter of ascites fluid will be treated using the following protocol. Before treatment, a pre-treatment PET/CT FMISO, FDG and MRI including F-19 will be performed to ascertain the status of the cancer. Laprascopic insertion of a scope will be used to remove the bulk of the ascites and concurrently a collagenase could be injected intravenously to reduce intratumoral pressure. A 60% perflubron emulsion mixed with the maximum soluble and tolerated amount of 2DG, and possibly collagenase, will be instilled to cover/submerge all of the peritoneal surface metastasis. The combination emulsion is then allowed to mix with the $CO_2$ gas of the laparascopic procedure. The abdomen will be supported with the combination for 2 hours. Approximately 4-24 hours post-op, the gas will be changed to 02 by having the patient breathe supplemental or hyperbaric $O_2$. Chemotherapeutics and localized radiation may be administered at this time independently or in combination. Following the ascribed procedure, a PET/CT with FMISO and FDG MRI with F-19 will be performed to ascertain the status of the cancer post-treatment.

Example 4. Pancreatic Cancer

A patient with a pancreatic mass in the head of the pancreas, which is surgically unresectable or where the patient chooses a less invasive treatment, will be treated with the following protocol. A pre-operative CT/PET scan using FDG and FMISO, as well as an MRI including a F-19 MRI and MRA of the biliary system will be conducted to assess the status of the cancer. Chemotherapy may be administered to the patient. For example, Gemcitabine with or without perflubron emulsion may be administered intravenously or intra-arterially. Alternatively, perflubron emulsion-cetuximab IRDye®700DX or 800CW IRDye may be given intravenous or intratumoral via endoscopic ultrasound. Open surgery, laparoscopic surgery, or endoscopy using ultrasound will be used to visualize the pancreas and slowly instill perflubron emulsion with 2DG and L-asparaginase to block the glucose and glutamine uptake by cancer cells. The combination will be instilled to completely fill the mass via convection and controlling reflux and overflow to the extent possible. Next, oxygen will be instilled for up to 20 minutes in combination with external beam radiation or radiation implantation (e.g. seeds or agent such as Rhenium 186 bonded to perflubron emulsion and administered). Chemotherapeutics and biologics such as antibody based therapies may be directly instilled along with the combination. Following the oxygen administration and PDT, the gas will be switched to $CO_2$ for the definitive kill dose for 10 to 120 minutes. Needle gas ports may be placed to monitor $CO_2$ saturation. Monitoring of $CO_2$ saturation ensures that normal tissue is not contaminated or minimally exposed to increase $CO_2$ saturation. Devices such as near infrared imaging or other novel instruments may be used to track $CO_2$ position. A follow-up PET/CT and Mill will be performed to analyze metabolic and structural changes.

The invention illustratively disclosed herein suitably may be practiced in the absence of any element, which is not specifically disclosed herein. It is apparent to those skilled in the art, however, that many changes, variations, modifications, other uses, and applications to the method are possible, and also changes, variations, modifications, other uses, and applications which do not depart from the spirit and scope of the invention are deemed to be covered by the invention, which is limited only by the claims which follow.

Example 5. Head and Neck Cancer

A clinically negative Head and Neck cancer patient generally has a 20-40% reoccurrence rate making selective or modified radical neck dissection desirable. In contrast, 60-80% of patients undergo unnecessary morbidity with this procedure (Peng et al., World J Surg Oncol. 2015; 13: 278. Published online 2015 Sep. 17). The use of perflubron emulsion (PFCE) in combination with IRDye® 700DX (LI-COR, Lincoln, NE) coupled to a ligand (e.g., RGD (arginine-glycine-aspartic acid), monoclonal antibody, and the like) injected intravenously and/or peritumorally preoperatively enables lymph node mapping by various means and subsequent photodynamic therapy (PDT) prior to surgery. The mapping means include, e.g., computed tomography (CT), magnetic resonance imaging (MRI; conventional and F19), Raman spectroscopy and probe confocal laser endomicroscopy (pCLE). The use of photodynamic therapy (PDT) on positive tumors, lymph channels (LC) and sentinel lymph nodes (SLN) sites prior to surgical manipulation or removal will mitigate the release of viable cancer cells during surgery. The PFCE-dye-target combination will also aid the evaluation of ex vivo tissue after surgical removal.

In some situations, preoperative near infrared imaging is limited due to location and depth. Indocyanine green (ICG) or a nonspecific dye (e.g., IRDye® 800CW) coupled to albumin is used intraoperatively to map the LC and SLN that do not necessarily contain tumor. A multispectral imaging device that detects 700 nm and 800 nm (and other wavelengths) of light are used. Initial studies utilize radioactive technetium and methylene blue, which are the current standard of care (SOC).

For example, a 65 year old male patient is referred who has a clinically negative exam except for a tongue mass. The patient may have buccal, floor of mouth or other head and neck masses. A PET/CT and MRI and LN biopsy and selective lymph node dissection is planned. The patient takes an oral solution or has his lesion sprayed or painted with perfluorooctyl bromide (PFOB) or PFCE combined with IRDye® 700DX RGD, PFOB/PFCE-nintedanib-IRDye® 700DX, or the like. After rinsing (or overnight in case of per os route of administration), the mass is scanned by pCLE.

If the image confirms cancer suspicions, then the patient is informed and the tumor site is peritumorally injected with the perflubron or perflubron emulsion combination at Day 1. After local anesthesia, up to four (4) peritumoral sites after local anesthesia on Day 1 in clinic with 0.5-4 ml PFCE-IRDye® 700DX-RGD (or the like). In some cases, the practitioner may opt for intratumoral injection then PDT and biopsy for histology at the first referred clinic visit. In those cases, the referring provider has already transmitted a photo to the Head and Neck surgeon and the patient had been advised to have the oral or topical perflubron emulsion-IR700 or 800 one to three days prior to appointment based on the appearance.

On Day 3 a non-contrast CT and MRI Head and Neck (MRI could include F19) and transcutaneous near infrared imaging (NIR) or MSOT is performed. The patient then undergoes PDT of the tumor and identified LC and SLN followed by biopsy if not already completed. The patient is then scheduled for surgery and all positive sites subjected to PDT prior to removal. A follow up baseline MRI at about 2 weeks is expected to reveal PFCE fading and repeat NIR/MSOT imaging to be negative.

This protocol is expected to eliminate the need to preoperatively inject the patient peritumorally with technetium (Tc) and methylene blue. ICG or similar nonspecific NIR (e.g., IRDye® 800CW-albumin) would be used to map non-specific LC and SLN. A 700 nm and 800 nm laser with sufficient power is used to treat the primary tumor, all LC and SLN and/or nearby negative nodes with PDT prior to surgical manipulation to avoid spread of tumor. The PDT is not expected to perturb the pCLE or surgical pathologist's evaluation.

Example 6. Routine Colonoscopy

The difficulty in identifying and treating colon cancer is expected to be improved with new image guided and treatment for minimally invasive procedures such as colonoscopy, bronchoscopy, cystoscopy or similar limited invasive applications. A patient with a mass or suspected mass is administered a PFOB or PFCE combined with a nonspecific or a specific fluorescent dye orally, instilled, intravenously, aerosolized or the like. Nonspecific agents such as indocyanine green or 5-aminoallyl, or specific targeted therapies such as monoclonal antibodies and small molecule inhibitors (e.g., nintedanib, afatinib and the like) may be used. The patient then undergoes an image guided procedure within about one to three days followed by photodynamic therapy prior to biopsy and evaluation for sentinel lymph node and lymphatic channels.

The combined anti-fibroblast, anti-macrophage and/or anti-inflammatory activity plus the improved vehicle, added oxygenation potential and imaging with Raman spectroscopy or stimulated Raman spectroscopy, pCLE, NIR, MRI (preferably F-19) and CT benefits the work up, treatment and follow-up. This process also encompasses theranostic procedures (diagnostic+therapeutic) that includes pre- and post-biopsy photodynamic therapy (PDT).

In one example, a 50 year old male patient who needs a routine colonoscopy undergoes a colonoscopy preparation. Following the slowing of loose stools approximately six hours later, the patient drinks about 100 ml of a PFOB- or PFCE-IRDye® 700DX-nintedanib labeled product. The next day at colonoscopy, the patient is started on 100% 02 to "load" the perflubron or perflubron emulsion before $CO_2$ insufflation. A fluorescent and Raman detector fixed to the scope or placed down the working channel is used to identify cancerous lesions. Since 5% of nintedanib is absorbed, 95% is available intraluminal. The perflubron or perflubron emulsion enhances the uptake of the nintedanib by the tumor relative to nintedanib alone. Afatinib, Regorafenib or other agent and or local spray maybe substituted for the nintedanib. Near infrared imaging of the lumen and nearby lymphatics accessible during the colonoscopy is also performed.

Prior to biopsy, the patient undergoes PDT followed by biopsy and then a peritumoral injection of the same product. Once the biopsy confirms invasive cancer, a CT/MRI Abdomen/Pelvis is completed to view the lymphatics for use during a near term laparoscopic procedure. Prior to or at time of laparoscopy, the patient is administered concurrent ICG and/or Tc to image the non-specific areas. If a multi-spectral detector is not available, then treatment of all lymphatic channels and lymph nodes is performed prior to biopsy or surgical manipulation. A reduction in tumor re-occurrence in the lymph node basin and lymphatic channels harboring in transit tumor is expected. Panitumumab-IRDye-800 CW is more specific than ICG and deeper than IRDye-700 ICG, and Tc may allow visualization but of shorter duration and non-specific. PDT of occult disease can be performed, but aims to treat specifically targeted cancer not ICG.

In another example, a 70 kg 55 year old male presents for routine screening colonoscopy. He drinks 200 ml of neat perflubron after he completes his colon preparation. The next day the colonoscope is inserted and a Raman spectral unit is used to navigate and scan the colon surface until the light encounters 3 concentrated areas of carbon-fluorine bond (C—F) signal. The Raman spectra PFOB is identified is then that scope is removed and a probe confocal endomicroscopy (pCLE) probe is inserted. The identified area is subjected to pCLE to visualize early cancer lesions. The early cancer lesions are treated with photo dynamic therapy (PDT), removed and sent for pathological confirmation.

This procedure allows a more sensitive method of screening using Raman spectroscopy immediately followed by diagnosis (pCLE) and subsequent treatment (PDT) all within the same procedure thereby reducing cost, complications and time. This protocol can be carried out in multiple other endoscopic or similar procedures such as screening for oral cancer, esophagus, gastric, colon, breast, pancreatic, lung, bladder and peritoneum among others. Current commercial units such as the Verisante AURA™ or those built by companies such as &W Tek may be used in the practice of the invention, including numerous other and as yet undiscovered detectors using a Raman signature of perfluorocarbons.

Example 7. Patient with a Lung Mass

In one example, a 60 year old smoker with an 8 mm lung mass in the right upper lobe undergoes CT/PET with a maximum standardized uptake value (SUV) of 2.1. The patient is recommended for a follow-up CT scan in 4-6 months and is given 100 ml PFCE-IRDye® 700DX or 800CW-cetuximab or afatinib via oral solution or 20 ml nebulized application on Day 1. At bronchoscopy, Raman spectroscopy and fluorescent detection is performed using navigational equipment (e.g., SUPERDIMENSION™ [superDimension, Inc., Minneapolis, MN], SPIN Thoracic [Veran Medical Technologies, Inc., St. Louis, MO], or LUNGPOINT® VBN [Broncus Medical, Inc., San Jose, CA]). A laser is used to detect and aid guidance to the lesion and a subsequent increase in power is delivered to perform PDT prior to biopsy. Lymph nodes and channels are inspected where possible, and PDT is performed. A post PDT peritumoral injection is performed. The patient follows up with video-assisted thoracoscopic surgery (VATS) after the biopsy is evaluated. PDT is repeated before and after surgery in all lymph channels and lymph nodes using ICG for detection and treatment.

Example 8. Patient with a Bladder Mass

In one example, a 70 year old smoker with hematuria (high pre-test possibility for cancer) is seen on Day 1 and the clinic cystoscopy is suspicious for cancer. In some cases, the patient could have been administered an oral, intravesical, intravenous, aerosolized solution of PFCE-dye-ligand prior to cystoscopy. The patient's lesion is peritumorally injected with PFCE-IRDye® 700 DX Cetuximab. On Day 3 an MRI/CT abdomen pelvis is performed. On Day 4 a laparoscopy and cystoscopy using NIR is performed. ICG or IRDye® 800CW can be used to navigate the lymphatics using an 800 nm detector during laparoscopy.

Example 9. Melanoma and Non-Melanoma Skin Conditions

In one example, a 42 year old with a suspicious black spreading lesion is referred for evaluation. A PFCE-IRDye® 700DX-RGD spray or topical is applied to the lesion, rinsed and examined by pCLE. If direct pCLE evaluation suggests cancer, then the patient is informed and by pressure-driven convection, intratumoral, intravenous, or peritumoral injected with the PFCE-IRDye® 700DX-RGD product. The patient follows up two to four days later for (1) an MRI F-19, (2) CT/PET RGD (or nintedanib or the like) and NIR, (3) MSOT, (4) PDT and then (5) surgical resection of all positive areas. Non-specific ICG or IRDye® 800CW is used to map the tissue in real time. Raman spectroscopy may be used to observe the C—F bonds in the tumor area first.

Example 10. Breast Mass

In one example, a suspicious lesion is seen in a 50 year old female during a routine mammogram. The patient is orally, intravenously, or intratumorally administered PFCE/PFOB-IRDye® 700DX (or 800CW)-nintedanib prior to being subject to ultrasound guided breast biopsy. A 19 G instrument enabling a pCLE catheter to be passed to the edge of the mass is used. If the mass is observed to be cancer-positive, then the mass is treated with PDT, followed by peritumoral injection with the PFCE/PFOB-IRDye® 700DX-nintedanib that was previously administered, followed by tumor-only PDT and biopsy. If the biopsy is positive, the patient is subjected to MRI F-19 and CT/PET nintedanib, and MSOT. The patient is then subjected to PDT of mass, LC and SLN prior to resection of the mass. Raman spectroscopy may be used to observe the C—F bonds in the tumor area first.

Example 11. Ovarian Cancer

In one example, a 55 year old female is referred for ascites. A CT abdomen and pelvis scan reveals "caking" over the omentum. Interventional Radiology is requested to remove fluid for diagnostic and therapeutic purposes. After obtaining a large volume of ascites fluid, the fluid is mixed ex vivo with PFCE/PFOB-IRDye® 700DX-RGD and imaged. If the 700 nm signal is positive in the ascites, the patient is injected with 200 ml of the same PFCE/PFOB-IRDye® 700DX-RGD composition and subjected to CT/PET RGD or nintedanib/afatinib, MRI and NIR/MSOT. Two to four days later, the abdominal/pelvic cavity is subjected to PDT and surgical debulking is performed. A laser diode left in place for subsequent PDT.

Example 12. Additional Cancers

A patient with prostate cancer suspicion is orally administered a PFCE/PFOB-IRDye® 700DX-target moiety composition. The prostate is subjected to PDT prior to prostate biopsy to prevent inadvertent release of potential viable tumor cells. The target moiety is a prostate cancer antigen-binding protein, an RGD peptide, a TKI such as nintedanib or afatinib, or the like.

A patient with glioblastoma suspicion is orally administered a PFCE/PFOB-IRDye® 700DX-target moiety composition. If the prospective lesion is fluorescent positive, the lesion is peritumorally injected with the same composition and subjected to PDT prior to biopsy. Follow up MRI, CT/PET RGD and PDT is performed prior to tissue resection. The target moiety is a glioblastoma antigen-binding protein, an RGD peptide, a TKI such as nintedanib or afatinib, or the like.

A patient with pancreatic cancer suspicion is orally administered a PFCE/PFOB-IRDye® 700DX-target moiety composition. If the prospective lesion is fluorescent positive, the lesion is peritumorally injected with the same composition and subjected to PDT prior to pancreatic biopsy. Follow up MRI, CT/PET RGD and PDT is performed prior to tissue resection. The target moiety is a pancreatic cancer antigen-binding protein, an RGD peptide, a TKI such as nintedanib or afatinib, or the like.

Example 13. Barrett's Esophagus and Other Esophageal Indications

In preparation of a patient in need of upper gastrointestinal endoscopy (EGD) for Barrett's esophagus or other upper GI dysplasia, hyperplasia or pre-cancer condition, the patient drinks Perflubron (e.g., 0.5-9 ml/kg) 0.25-24 hours prior to procedure or instills the perfluorooctyl bromide (a.k.a. perflubron) (PFOB) or perflubron emulsion (PFCE) at time of EGD. The perflubron or perflubron emulsion is applied over the top of the mucosal surface in a sufficient amount to reduce mucus. Prior art methods employ N-acetylcysteine (NAC), which may impede subsequent photodynamic therapy (PDT). Here, we use of perflubron or perflubron emulsion enhances PDT. PFOB/PFCE also enables the use of Raman spectroscopy and similar techniques for visualizing fibroblasts and stroma.

While not wishing to be bound by theory, perflubron or perflubron emulsion, which is denser than water and has a significant elevated spreading coefficient, can distribute below the mucus layer. The PFOB smooths out the epithelial surface thereby reducing the scatter from the upcoming laser.

Example 14. Tumor to Background Ratio

HCT 116 tumor-bearing mice (n=3) were injected via tail vein with 200 μg of cetuximab-IRDye®-800CW (1) with 30% perflubron as an emulsion (PFCE) (100 μL of cetuximab-IRDye® 800CW at 2 mg/ml was combined with and 100 μL of 60% Perflubron emulsion to make it a 30% solution of Perflubron emulsion), or (2) without PFCE, in a total volume of 200 μL. The mice were then subjected to in vivo imaging at day 3 post-injection using a Pearl® Trilogy Small Animal imaging System (LI-COR Biosciences, Lincoln, NE). The tumor to background ratio (TBR) for each tumor was calculated. The results are depicted in Table 1. The inclusion of 30% PFCE resulted in a 34% (p=0.05) increase in TBR.

TABLE 1

| In Vivo TBR | |
|---|---|
| Drug combination | TBR at 3 days post-injection |
| Cetuximab-IR800 (w/out PFCE) | 3.6 (sd = 0.4) |
| Cetuximab-IR800 + PFCE | 4.8 (sd = 0.9) |

Tumors (HCT116) and other tissues were then removed from the mice (n=3) and the tumors and tissues were subjected to ex vivo Pearl® imaging. The tumor to liver ratio for each tumor was calculated. The results are depicted in Table 2. The inclusion of 30% PFCE resulted in an 85% (p=0.01) increase in tumor to liver ratio.

TABLE 2

| Ex Vivo Tumor to Liver Ratio | |
|---|---|
| Drug combination | TBR at 3 days post-injection |
| Cetuximab-IR800 (w/out PFCE) | 2.5 (sd = 0.6) |
| Cetuximab-IR800 + PFCE | 4.6 (sd = 0.6) |

Example 15. Tumor Labeling—Stromal Cells and Cancer Cells

Figure 2:
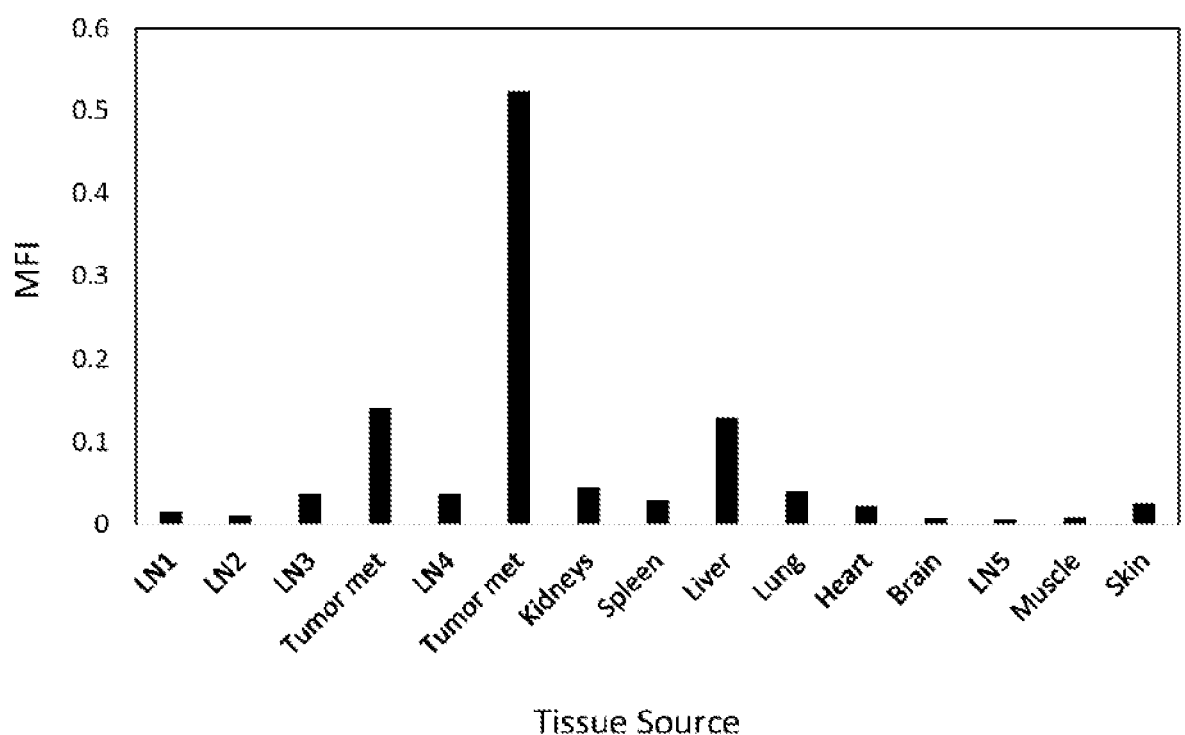
FIG. 2 depicts a bar histogram depicting mean fluorescence intensity in arbitrary units at 800 nm as a function of tissue uptake of IRDye®-800CW-labeled cetuximab. The X-axis depicts tissues, where LN=lymph node.

Tumors and other tissues were removed from tumor bearing mice 4 days after tail vein injection with PFCE+cetuximab-IR800 treated (200 μL at 200 μg cetuximab-IR800). The dissected tissues were lymph nodes 1~4 (LN), tumor metastasis, tumor, kidneys, spleen, liver, lung, heart, brain, muscle, and skin. The excised tissues from those animals treated with PFCE+cetuximab-IR800 were subjected to ex vivo Pearl® imaging and the fluorescence intensities at 700 nm and 800 nm were determined. FIG. 1 depicts the mean fluorescence intensity for each tissue at 700 nm, which is attributed to the reflectance due to the PFCE. Here, the tumor showed an approximately 4-fold greater fluorescence intensity at 700 nm than liver tissue. FIG. 2 depicts the mean fluorescence intensity for each tissue at 800 nm, which is attributed to the localization of the cetuximab-IR800 NIR-C. Here, the tumor showed an approximately 4-fold greater fluorescence intensity at 800 nm than liver tissue.

Example 16. In Vivo Tumor Eradication

A dog with extensive metastatic pulmonary osteosarcoma was treated with 60% perflubron emulsion (PFCE) containing 9 mg/mL gemcitabine (GCB) (PFCE-GCB=1000 mg GCB in 110 mL 60% perflubron emulsion). Aerosolized PFCE-GCB was delivered to the lungs of the dog twice weekly using an AeroTech™ II nebulizer (Biodex Medical Systems, Inc., Shirley, NY). The dog showed no side effects during the treatment.

At 6 weeks, the dog showed a complete response of pulmonary metastasis. And after 6 months of the twice-weekly treatment, there were no side effects and no lung metastasis returned. Treatment was discontinued at 6 months. After more than 1 year, no pulmonary metastasis were observed when the dog was necropsied.

Control dogs (n=50) received gemcitabine alone. None of the control dogs showed durable tumor eradication as observed in the PFCE-GCB treated dog, since tumors returned in all control cases.

Example 17. Improved Tumor and Tumor Field Imaging and Therapy

Perflubron emulsion improves fluorescent tag imaging for both diagnosis and treatment (theranostic) uses by increasing tumor to background ratio (TBR).

A middle aged man (about 90 kg±10 kg) with a 3 cm tongue mass suspected of head and neck squamous cell cancer is given by intravenous injection 30% Perflubron emulsion—cetuximab-IRDye® 800CW (100 mg) on Day-One. Before surgery, the patient is imaged by CT or MM, and also near infrared imaging. On Day-Four the man is subjected to surgery. The 800 nm image is significantly brighter (about 85% increase in fluorescence) and the borders of the tumor more clear (than a patient having been administered cetuximab-IRDye® 800CW (100 mg) without Perflubron emulsion.

After resection of the main tongue mass, the tumor area is subjected to intraoperative fluoroscopy or CT or conventional MRI to confirm whether all gross perflubron emulsion has been removed. The presence of perflubron indicates that some cancer associated fibroblasts and macrophages still remain. The absence of perflubron indicates that the cancer associated fibroblasts and macrophages have been removed. The immediate peritumoral resection can be further evaluated by Raman spectroscopy to identify the presence of C—F bonds in microscopic cancer associated fibroblasts and macrophages, which are surrogates of cancer. The C—F detected foci can be further examined by probe confocal endomicroscopy to detect fluorescence from the IRDye®800CW-cetuximab, and then biopsied to confirm.

Field sterilization based on the locations identified can be performed using PDT.

What is claimed is:

1. A method of killing a cell comprising:
   contacting the cell with a fluorochemical composition, wherein the fluorochemical composition comprises a perfluorocarbon, an emulsion agent, a therapeutic gas, a fluorescent label, and a chemotherapy agent.

2. The method of claim 1, wherein the chemotherapy agent is selected from the group consisting of alemtuzumab, bevacizumab, cetuximab, gemtuzumab ozogamicin, ibritumomab tiuxetan, ofatumumab, panitumumab, rituximab, tositumomab, trastuzumab, and trastuzumab DM1.

3. The method of claim 1, wherein the fluorochemical composition further comprises a bioactive agent.

4. The method of claim 1, further comprising contacting the cell with a secondary treatment.

5. The method of claim 4, wherein said secondary treatment is selected from the group consisting of surgery, radiation, sound, and light.

6. The method of claim 1, further comprising contacting the cell with any one or more of radiation, light, and sound.

7. The method of claim 1, wherein said label emits near infrared light.

8. The method of claim 7, wherein said near infrared light is about 700 nm or 800 nm.

9. A method of killing a cell comprising:
   contacting the cell with a fluorochemical composition, wherein the fluorochemical composition comprises a perfluorocarbon, an emulsion agent, a therapeutic gas, a fluorescent label, and cetuximab.

10. A method of killing a cell comprising:
    contacting the cell with a fluorochemical composition, wherein the fluorochemical composition comprises a perfluorocarbon, an emulsion agent, a therapeutic gas, and a fluorescent label:
    wherein the fluorochemical composition further comprises a biological molecule; and
    wherein said fluorescent label is covalently linked to said biological molecule.

11. A method of killing a cell comprising:
    contacting the cell with a fluorochemical composition, wherein the fluorochemical composition comprises a perfluorocarbon, an emulsion agent, a therapeutic gas, a fluorescent label, and gemcitabine.

12. A method of killing a cell comprising:
    contacting a stroma cell with a fluorochemical composition, wherein the fluorochemical composition comprises a perfluorocarbon, an emulsion agent, a therapeutic gas, and a fluorescent label.

13. A method of killing a cell comprising:
    contacting the cell with a fluorochemical composition, wherein the fluorochemical composition consists of perflubron, an emulsion agent, oxygen, a bioactive agent, and a fluorescent label, wherein said bioactive agent and said fluorescent label are not conjugated; and
    contacting the cell with any one or more of radiation, light, and sound,
    wherein the cell is a stroma cell in a patient or a cancer cell in a patient.

14. A method of killing a cell comprising:
    contacting the cell with a fluorochemical composition, wherein the fluorochemical composition comprises a perfluorocarbon, an emulsion agent, a therapeutic gas, a bioactive agent, and a fluorescent label;
    wherein the cell is a cancer cell in a patient; and
    wherein said bioactive agent is gemcitabine and said fluorescent label emits near infrared light.

15. A method of killing a cell comprising:
    contacting the cell with a fluorochemical composition, wherein the fluorochemical composition consists of perflubron, an emulsion agent, oxygen, and a fluorescent label; and
    contacting the cell with any one or more of radiation, light, and sound,
    wherein the cell is a stroma cell in a patient or a cancer cell in a patient.

16. A method of treating caner in a patient comprising:
    administering a composition comprising perflubron, a photosensitizer, and gemcitabine to the patient; and
    treating the patient with a secondary therapy.

17. The method of claim 16, wherein said photosensitizer is a fluorescent label.

18. The method of claim 16, wherein said photosensitizer emits near infrared light.

19. The method of claim 16, wherein the composition is administered to the patient via a route selected from the group consisting of intravenous, intraocular, intratracheal, intratumoral, oral, rectal, topical, intramuscular, intraarterial, intrahepatic, intrathoracic, intrathecal, intracranial, intraperitoneal, intrapancreatic, intrapulmonary, gastrointestinal, and subcutaneous.

20. The method of claim 16, wherein the composition is a liquid, an aerosolized liquid, a dry powder, or an aerosolized dry powder.

21. A method of treating cancer in a patient comprising:
administering a composition comprising perflubron and a fluorescent label to the patient; and
treating the patient with a secondary therapy;
wherein said fluorescent label is conjugated to an antibody.

22. The method of claim 21, wherein said antibody is cetuximab or panitumumab.

23. A method of treating cancer in a patient comprising:
administering a composition comprising perflubron and a photosensitizer to the patient; and
treating the patient with a secondary therapy;
wherein said secondary therapy comprises sound therapy.

24. A method of treating cancer in a patient comprising:
administering a composition comprising perflubron and a photosensitizer to the patient; and
treating the patient with a secondary therapy;
wherein said secondary therapy comprises photodynamic therapy.

25. A method of treating cancer in a patient comprising:
administering a composition comprising perflubron and a photosensitizer to the patient; and
treating the patient with a secondary therapy;
wherein said secondary therapy comprises radiation therapy.

\* \* \* \* \*